(12) United States Patent
Nuutinen et al.

(10) Patent No.: US 9,902,904 B2
(45) Date of Patent: Feb. 27, 2018

(54) TAGGED SCALE INHIBITING POLYMER COMPOSITIONS AND METHODS OF INHIBITING SCALE FORMATION

(71) Applicant: Kemira Oyj, Helsinki (FI)

(72) Inventors: Vesa Nuutinen, Helsinki (FI); Susanna Toivonen, Espoo (FI)

(73) Assignee: Kemira Oyj, Helsinki (FI)

( * ) Notice: Subject to any disclaimer, the term of this patent is extended or adjusted under 35 U.S.C. 154(b) by 429 days.

(21) Appl. No.: 14/591,303

(22) Filed: Jan. 7, 2015

(65) Prior Publication Data

US 2015/0184069 A1 Jul. 2, 2015

Related U.S. Application Data

(63) Continuation of application No. PCT/EP2013/064634, filed on Jul. 10, 2013.

(Continued)

(51) Int. Cl.
| | |
|---|---|
| *C02F 5/12* | (2006.01) |
| *C09K 11/06* | (2006.01) |
| *C08F 226/00* | (2006.01) |
| *G01N 21/64* | (2006.01) |
| *C02F 103/02* | (2006.01) |

(Continued)

(52) U.S. Cl.
CPC ............... *C09K 11/06* (2013.01); *C02F 5/12* (2013.01); *C08F 226/00* (2013.01); *G01N 21/64* (2013.01); *C02F 2103/023* (2013.01); *C02F 2103/10* (2013.01); *C02F 2103/16* (2013.01); *C02F 2103/28* (2013.01); *C02F 2103/32* (2013.01); *C02F 2103/365* (2013.01); *C02F 2303/22* (2013.01); *C09K 2211/1018* (2013.01); *G01N 2201/061* (2013.01)

(58) Field of Classification Search
CPC ............... C09K 11/06; C09K 2211/1018; G01N 21/64; G01N 2201/061; C02F 5/12; C02F 2103/023; C02F 2103/10; C02F 2103/16; C02F 2103/28; C02F 2103/32; C02F 2103/365; C02F 2303/22; C08F 226/00

See application file for complete search history.

(56) References Cited

U.S. PATENT DOCUMENTS

| | | |
|---|---|---|
| 2,260,420 A | 10/1941 | Young et al. |
| 2006/0254985 A1 | 11/2006 | Morris |
| 2009/0053825 A1* | 2/2009 | Takeuchi ................ B01J 20/26 436/501 |

FOREIGN PATENT DOCUMENTS

| | | |
|---|---|---|
| WO | WO 2005/000747 | 1/2005 |
| WO | 2013/028332 | 2/2013 |

OTHER PUBLICATIONS

International Search Report for corresponding international application PCT/EP2013/064634, dated Aug. 2, 2013.

* cited by examiner

*Primary Examiner* — Taiwo Oladapo
(74) *Attorney, Agent, or Firm* — King & Spalding

(57) ABSTRACT

Scale-inhibiting polymers comprising one or more scale-inhibiting units and one or more tagging units, wherein each tagging unit is formed from a compound of Formula I, II, III, or IV, or a salt, hydrate, salt hydrate, stereoisomer, dehydrate or derivative thereof. Scale-inhibiting compositions comprising the scale-inhibiting polymers, processes for determining a concentration of a scale-inhibiting polymer for inhibiting scale formation, and methods for preventing or controlling scale formation in systems comprising fluid circulation with the scale-inhibiting polymers are also disclosed herein.

52 Claims, 10 Drawing Sheets

Related U.S. Application Data

(60) Provisional application No. 61/669,908, filed on Jul. 10, 2012, provisional application No. 61/821,512, filed on May 9, 2013, provisional application No. 61/824,694, filed on May 17, 2013.

(51) Int. Cl.
*C02F 103/10* (2006.01)
*C02F 103/16* (2006.01)
*C02F 103/28* (2006.01)
*C02F 103/32* (2006.01)
*C02F 103/36* (2006.01)

TAGGED SCALE INHIBITING POLYMER COMPOSITIONS AND METHODS OF INHIBITING SCALE FORMATION

CROSS REFERENCE TO RELATED APPLICATIONS

This application is a continuation of International Application No. PCT/EP2013/064634, filed Jul. 10, 2013, which claims priority to U.S. Provisional Patent Application No. 61/669,908, filed Jul. 10, 2012; U.S. Provisional Patent Application No. 61/821,512, filed May 9, 2013 and U.S. Provisional Patent Application No. 61/824,694, filed May 17, 2013.

FIELD OF THE ART

The present disclosure generally relates to tagged scale-inhibiting polymer compositions and methods of inhibiting scale formation.

BACKGROUND

Scale formation or deposition can produce numerous problems across a wide range of applications. Exemplary problems involving scale formation include but are not limited to reduced heat transfer efficiency, flow restrictions and plugging, underdeposit corrosion, microbiological growth, cleaning costs, equipment damage and failure. Generally, scale formation adversely impacts many companies by contributing to lost production, increasing operating costs, and increasing capital equipment costs.

Many minerals can produce mineral scale, for example calcium carbonate, calcium sulfate, barium sulfate, calcium oxalate, calcium phosphate, silica, calcium silicate, magnesium silicate, fluorosilicate, aluminosilicate, strontium sulfate, calcium fluoride, magnesium hydroxide, and various iron or manganese compounds. The compositions and methods disclosed herein may be used to reduce or inhibit the formation of one or more types of scale. In exemplary embodiments, the scale-inhibiting polymer can be used as a scale inhibitor in any industrial water system where a scale inhibitor is needed. Suitable industrial water systems, include, without limitation, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

Scale-inhibiting polymers are often used in water treatment and oil field applications to minimize and/or prevent scale deposition. The deposition of scale can occur in the transport of aqueous mixtures and in subterranean rock formations due to the presence of water bearing alkaline earth metal cations such as calcium, barium, strontium, and the like as well as the presence of anions such as phosphate, sulfates, carbonates, silicates and the like. When these ions are in sufficient concentrations, a precipitate can form that builds up on interior surfaces of the conduits used for transport or in the subterranean rock formations, which restrict flow of the media of interest, e.g., water or oil. In oilfield applications, scales that are commonly formed include calcium sulfate, barium sulfate, and/or calcium carbonate that are generally formed in the fresh waters or brines used in well stimulation and the like as a result of increased concentrations of these particular ions, the water pH, pressures, and temperatures. In addition, calcium phosphate can form from the phosphate chemistry that is commonly used to treat wells and pipes for corrosion. The buildup of these mineral precipitates can reduce or block flow in the conduits and rock formations as well as cause other problems. In many cases, the first warning of the existence of a significant scale deposit may be a decline in well performance. In these instances, scale removal techniques may become necessary. As a result, a potentially substantial cost including downtime is required lost to effect repair as a result of scaling.

Scale-inhibiting materials are often added directly to a fluid to be treated or applied to oil bearing rock formations such as by means of "squeeze treatment". A "squeeze" is an application of a treatment fluid or slurry into a treatment zone under pressure. In a squeeze application, the scale inhibitor may attach to the formation by chemical adsorption or by temperature-activated precipitation. When the well is put back into production, the scale inhibitor may leach out of the formation rock to treat the fluid. Some chemicals typically used in scale-inhibitor squeeze applications include phosphonated carboxylic acids or polymers.

The concentration of the scale inhibitor affects the effectiveness of the scale inhibitor. Each scale inhibitor has a predetermined "minimum inhibitor concentration" for a particular application. Above the minimum inhibitor concentration, scale formation may be effectively controlled. When the scale inhibitor concentration is below the minimum inhibitor concentration such as may occur during use, adsorption or degradation, additional amounts are then needed. For example, when a well is subjected to the squeeze application and then returned to operation, the concentration of the scale inhibitor in the produced fluids will diminish over time until such time that the scale inhibitor is at about or below the minimum inhibitor concentration. However, it can be difficult to determine when more scale inhibitor is needed and in which conduit or well it is needed. To address this problem, scale inhibitors may be tagged or labeled so that the presence or absence of the scale inhibitor can be readily detected. Scale inhibitor compounds have been tagged by introduction of specific atoms such as phosphorous or boron, which can be readily detected by inductively coupled plasma (ICP) analysis, thereby providing a means to detect the presence and/or concentration of the scale inhibitor.

BRIEF SUMMARY

Disclosed herein are scale-inhibiting polymers comprising one or more scale-inhibiting units and one or more tagging units, wherein each tagging unit is formed from a compound of Formula I, II, III, or IV, or a salt, hydrate, salt hydrate, stereoisomer, dehydrate or derivative thereof. Scale-inhibiting compositions comprising the scale-inhibiting polymers, processes for determining a concentration of a scale-inhibiting polymer for inhibiting scale formation, and methods for preventing or controlling scale formation in systems comprising fluid circulation with the scale-inhibiting polymers are also disclosed herein.

The disclosure may be understood more readily by reference to the following detailed description of the various features of the disclosure and the examples included therein.

DETAILED DESCRIPTION

Figure 1:
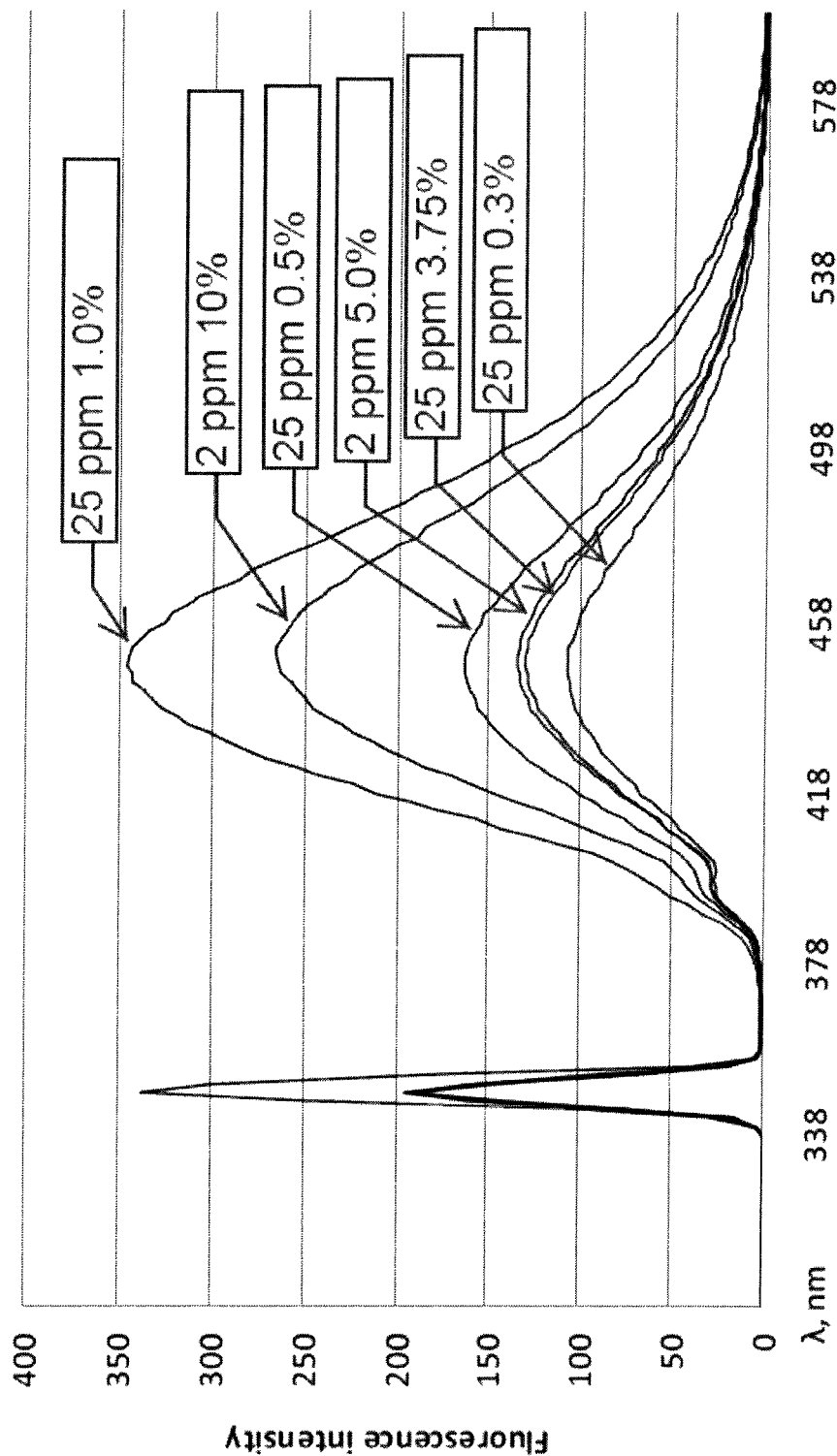
FIG. 1 shows fluorescence spectra of several exemplary quinine-tagged polymers at various incorporation levels and polymer concentration levels (measured in acidic media).

The present disclosure is generally directed to scale-inhibiting polymers, scale-inhibiting compositions and methods for inhibiting scale formation. The compositions generally include a scale-inhibiting polymer comprising a scale-inhibiting unit and a tagging unit. The tagging unit fluoresces at a predetermined wavelength, so that the fluorescence of the tagging unit can be used to determine the concentration of the scale-inhibiting polymer. In exemplary embodiments, the tagging unit includes a compound of Formula I, II, III, or IV or a salt, hydrate, salt hydrate, stereoisomer, dehydrate or derivative thereof, described herein.

The tagging unit, or tagging monomer, without substitution, has fluorescence emission maxima at about 410 to about 500, or about 440 to about 450 nanometers (nm), thereby providing the scale-inhibiting polymer with a means for monitoring the concentration of the scale inhibitor polymer at a wavelength.

In exemplary embodiments, the detection wavelength for the tagging monomer, for example quinine, may be different from the wavelength of other specific atoms or scale-inhibiting polymers tagged with one or more fluorescent moieties. Because of the difference in wavelength, the scale-inhibiting polymer including the tagging monomer can be differentiated from other detectable moieties, and can be used in multi-tagged systems.

In exemplary embodiments, the tagged scale-inhibiting polymers are obtainable by free radical polymerization of one or more scale-inhibiting units with one or more tagging units. In exemplary embodiments, scale-inhibiting polymers may be produced by polymerization of one or more types of monomer (including 2, 3, 4, or more different monomers) without restriction on the number of monomer units that are incorporated into the product provided that at least one of the monomers is a scale-inhibiting unit and at least one of the monomers is a tagging unit as described herein. In one embodiment, the scale-inhibiting polymer comprises one or more scale-inhibiting units and one or more tagging units as described herein. In certain embodiments, the scale-inhibiting polymer comprises two or more scale-inhibiting units and one or more tagging units as described herein.

As used herein, the terms "polymer," "polymers," "polymeric," and similar terms are used in their ordinary sense as understood by one skilled in the art, and thus may be used herein to refer to or describe a large molecule (or group of such molecules) that contains recurring units. Polymers may be formed in various ways, including by polymerizing monomers and/or by chemically modifying one or more recurring units of a precursor polymer. A polymer may be a "homopolymer" comprising substantially identical recurring units formed by, e.g., polymerizing a particular monomer. A polymer may be a "copolymer" comprising two or more different recurring units formed by, e.g., copolymerizing two or more different monomers, and/or by chemically modifying one or more recurring units of a precursor polymer. The term "terpolymer" may be used herein to refer to polymers containing three or more different recurring units.

The term "antiscalant" or "scale inhibitor" generally refers to chemicals that are applied at substoichiometric levels to interfere with crystal nucleation, growth, and agglomeration. As used herein, the terms "antiscalant," "antiscalants," "antiscale agent," "scale inhibitor" and similar terms are used in their ordinary sense as understood by one skilled in the art, and thus may be used herein to refer to or describe chemical compounds or compositions containing such compounds, where the compounds, when added to an aqueous system, reduce or inhibit the amount of scale and/or rate of formation of scale in the aqueous system, as compared to a system that does not contain the added chemical compound or composition. In this context, the terms "scale" or "mineral scale" refers to insoluble substances such as insoluble salts, that have a tendency to form in aqueous systems such as boiler water, cooling water, seawater (e.g. in oil platform applications), brackish water, oilfield water, municipal treatment plant water, paper mill water, mining water, and industrial treatment plant water.

The term "treatment of scale" will be understood by those skilled in the art to have a broad and customary meaning that includes using the antiscale compositions to reduce or inhibit the amount of scale and/or reduce the rate of formation of scale in various aqueous systems, as compared to comparable aqueous systems that do not contain the antiscale composition.

In exemplary embodiments, the one or more scale-inhibiting units is selected from the group consisting of: allylsulfonate salts, for example sodium allylsulfonate; acrylic acid; vinyl sulfonic acid or vinyl sulfonate salts; vinyl phosphoric acid or vinyl phosphonate salts; vinylidene diphosphonic acid or salts thereof; methacrylic acid; vinyl acetate; vinyl alcohol; vinyl chloride; unsaturated mono- or di-carboxylic acids or anhydrides such as maleic anhydride, maleic acid, fumaric acid, itaconic acid, aconitic acid, mesaconic acid, citraconic acid, crotonic acid, isocrontonic acid, angelic acid, and tiglic acid; vinyl chloride; styrene-p-sulfonic acid, or styrene sulfonates salts; acrylamido-2- methylpropanesulfonic acid (AMPS); hydroxyphosphonoacetic acid (HPA); hypophosphorus acids; acrylamides; propargyl alcohol having formula HC≡C—CH₂—OH; butyr-1,4-diol, and mixtures thereof. In a particular embodiment, two or more types of scale-inhibiting monomer are used, for example sodium allylsulfonate and maleic acid, or sodium allylsulfonate and maleic anhydride.

In exemplary embodiments, the tagging unit, or tagging monomer, is formed from a compound of Formula I, II, III, or IV:

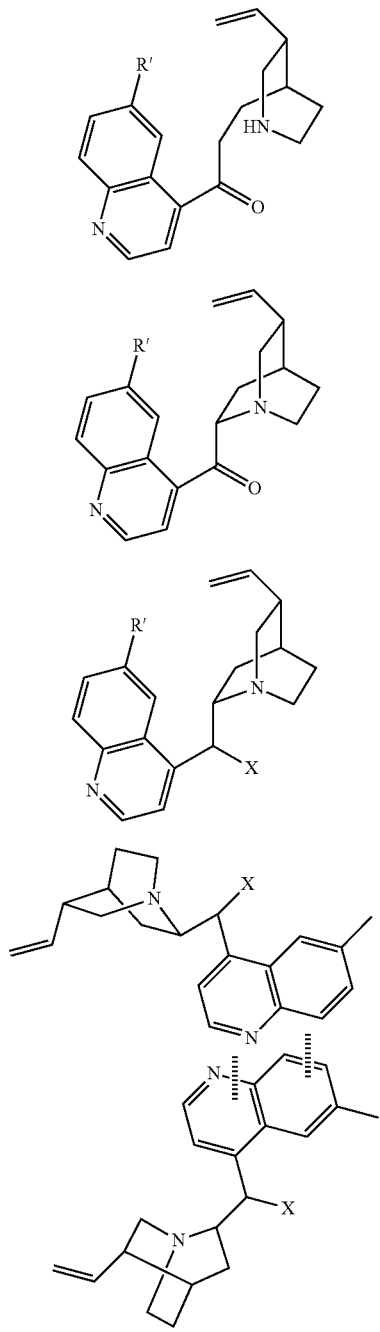

Formula I

Formula II

Formula III

Formula IV wherein each R' is independently R, OR, NRC(S)NR₂, or NRC(O)NR₂;

each R is independently H, $C_1$-$C_6$ alkyl, $C_2$-$C_6$ alkenyl, $C_6$-$C_{14}$ aryl, or $C_7$-$C_{20}$ aralkyl;

each X is independently OR, NR₂, NRC(S)NR₂, NRC(O)NR₂, NRSO₂R, or

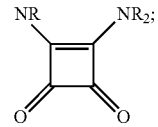

and wherein each alkyl or aryl group may be optionally independently substituted with one or more halo, $C_1$-$C_6$ alkyl, or $C_1$-$C_6$ haloalkyl substituents; or a salt, hydrate, salt hydrate, stereoisomer, dehydrate or derivative thereof.

In exemplary embodiments, the tagging unit is formed from a compound of Formula I or II:

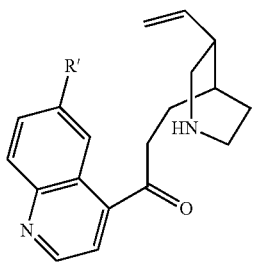

Formula I

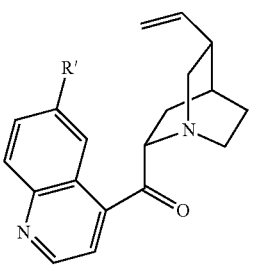

Formula II wherein each R' is independently R, OR, NRC(S)NR₂, or NRC(O)NR₂;

each R is independently H, $C_1$-$C_6$ alkyl, $C_2$-$C_6$ alkenyl, $C_6$-$C_{14}$ aryl, or $C_7$-$C_{20}$ aralkyl; and wherein each alkyl or aryl group may be optionally independently substituted with one or more halo, $C_1$-$C_6$ alkyl, or $C_1$-$C_6$ haloalkyl substituents; or a salt, hydrate, salt hydrate, stereoisomer, dehydrate or derivative thereof.

In exemplary embodiments, the tagging unit is a salt or salt hydrate of a compound of Formula I, II, III or IV, for example a hydrochloride, dihydrochloride, sulfate, bisulfate, or gluconate salt, or hydrate thereof. In exemplary embodiments, the tagging unit is a hydrate of a compound of Formula I, II, III or IV. In exemplary embodiments, the tagging unit is a stereoisomer of a compound of Formula I, II, III or IV. In exemplary embodiments, the tagging unit is a dehydrate of a compound of Formula I, II, III or IV. In exemplary embodiments, the tagging unit is a derivative of a compound of Formula I, II, III or IV, for example a derivative formed from the addition of acid and heat to the compound of Formula I, II, III or IV.

In exemplary embodiments, the tagging unit is a compound of Formula I, or a salt, hydrate, salt hydrate, stereoisomer, dehydrate or derivative thereof. In exemplary embodiments, the tagging unit is a compound of Formula II, or a salt, hydrate, salt hydrate, stereoisomer, dehydrate or derivative thereof. In exemplary embodiments, the tagging unit is a compound of Formula III, or a salt, hydrate, salt hydrate, stereoisomer, dehydrate or derivative thereof. In exemplary embodiments, the tagging unit is a compound of Formula IV, or a salt, hydrate, salt hydrate, stereoisomer, dehydrate or derivative thereof.

In one embodiment, R is H. In one embodiment, R is $C_1$-$C_6$ alkyl, for example methyl, ethyl, propyl, butyl, pentyl, or hexyl. In one embodiment, R is $C_2$-$C_6$ alkenyl, for example ethenyl, propenyl, butenyl, pentenyl, or hexenyl. In one embodiment, R is $C_6$-$C_{14}$ aryl, for example phenyl, naphthyl, phenanthrenyl, or anthracenyl. In one embodiment, R is $C_7$-$C_{20}$ aralkyl, for example benzyl, phenylmethylene, naphthylmethylene, phenanthrenylmethylene, or anthracenylmethylene.

In one embodiment, one or more alkyl or aryl groups in substituted with one or more halo substituents, for example F, Cl, Br, or I. In one embodiment, one or more alkyl or aryl groups in substituted with one or more $C_1$-$C_6$ alkyl substituents, for example methyl, ethyl, propyl, butyl, pentyl, or hexyl. In one embodiment, one or more alkyl or aryl groups in substituted with one or more $C_1$-$C_6$ haloalkyl substituents, for example $CF_3$.

In one embodiment, R' is R. In one embodiment, R' is OR. In one embodiment, R' is $NRC(S)NR_2$. In one embodiment, R' is $NRC(O)NR_2$. In a particular embodiment, R' is H. In another particular embodiment, R is $O(C_1$-$C_6$ alkyl), for example methoxy.

In one embodiment, X is OR. In another embodiment, X is $NR_2$. In another embodiment, X is $NRC(S)NR_2$. In another embodiment, X is $NRC(O)NR_2$. In another embodiment, X is $NRSO_2R$. In another embodiment, X is

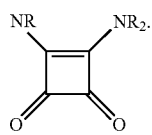

In a particular embodiment, X is OH.

In exemplary embodiments, the tagging unit may be cinchona alkaloid monomer, for example a quinicine monomer, a cinchonicine monomer, a quininone monomer, a cinchoninone monomer, a quinine monomer, a quinidine monomer, a cinchonine monomer, a cinchonidine monomer, or other cinchona alkaloid monomer.

(a)

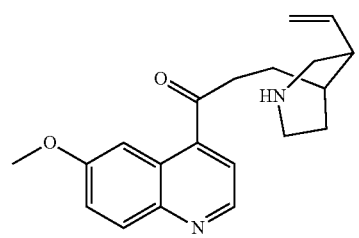

-continued (b)

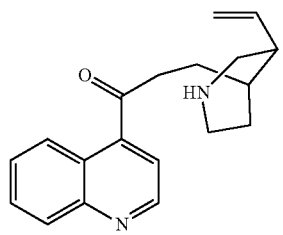

(c)

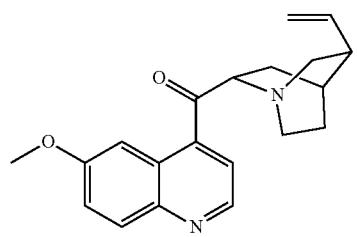

(d)

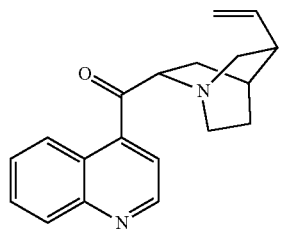

(e)

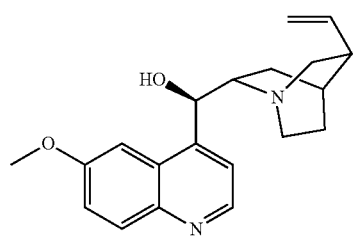

(f)

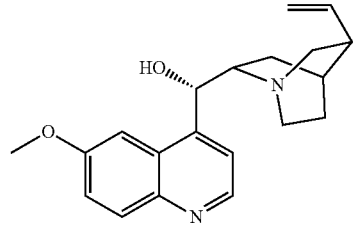

(g)

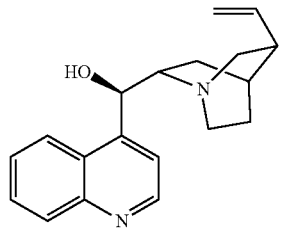

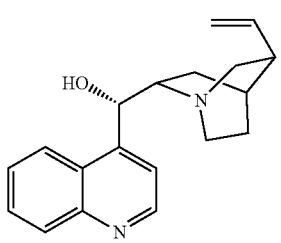
(h)

In the structures shown above, (a) is Quinicine; (b) is Cinchonicine; (c) is Quininone; (d) is Cinchoninone; (e) is Quinine; (f) is Quinidine; (g) is Cinchonidine; and (h) is Cinchonine.

In exemplary embodiments, the tagging unit is a quinicine monomer, which may be selected from quinicine, quinicine salts, quinicine hydrates, quinicine salt hydrates, any form of quinicine that is commercially available, or a derivative of quinicine which does not adversely affect the ability of the quinicine moiety to fluoresce or to undergo polymerization.

In exemplary embodiments, the tagging unit is a cinchonicine monomer, which may be selected from cinchonicine, cinchonicine salts, cinchonicine hydrates, cinchonicine salt hydrates, any form of cinchonicine that is commercially available, or a derivative of cinchonicine which does not adversely affect the ability of the cinchonicine moiety to fluoresce or to undergo polymerization.

In exemplary embodiments, the tagging unit is a quininone monomer, which may be selected from quininone, quininone salts, quininone hydrates, quininone salt hydrates, any form of quininone that is commercially available, or a derivative of quininone which does not adversely affect the ability of the quininone moiety to fluoresce or to undergo polymerization.

In exemplary embodiments, the tagging unit is a cinchoninone monomer, which may be selected from cinchoninone, cinchoninone salts, cinchoninone hydrates, cinchoninone salt hydrates, any form of cinchoninone that is commercially available, or a derivative of cinchoninone which does not adversely affect the ability of the cinchoninone moiety to fluoresce or to undergo polymerization.

In exemplary embodiments, the tagging unit is a quinine monomer, which may be selected from quinine, quinine salts, quinine hydrates, quinine salt hydrates, any form of quinine that is commercially available, or a derivative of quinine which does not adversely affect the ability of the quinine moiety to fluoresce or to undergo polymerization.

In exemplary embodiments, the tagging unit is a quinidine monomer, which may be selected from quinidine, quinidine salts, quinidine hydrates, quinidine salt hydrates, any form of quinidine that is commercially available, or a derivative of quinidine which does not adversely affect the ability of the quinidine moiety to fluoresce or to undergo polymerization.

In exemplary embodiments, the tagging unit is a cinchonine monomer, which may be selected from cinchonine, cinchonine salts, cinchonine hydrates, cinchonine salt hydrates, any form of cinchonine that is commercially available, or a derivative of cinchonine which does not adversely affect the ability of the cinchonine moiety to fluoresce or to undergo polymerization.

In exemplary embodiments, the tagging unit is a cinchonidine monomer, which may be selected from cinchonidine, cinchonidine salts, cinchonidine hydrates, cinchonidine salt hydrates, any form of cinchonidine that is commercially available, or a derivative of cinchonidine which does not adversely affect the ability of the cinchonidine moiety to fluoresce or to undergo polymerization.

In exemplary embodiments, the tagging unit is a compound formed from the addition of acid and/or heat to the compound of Formula III, compound of Formula IV, quinine monomer, quinidine monomer, cinchonine monomer, or cinchonidine monomer. For example, quinine or quinidine can be treated with acid and heat to prepare quinicine, quininone or mixtures thereof (see Scheme 1).

Scheme 1.

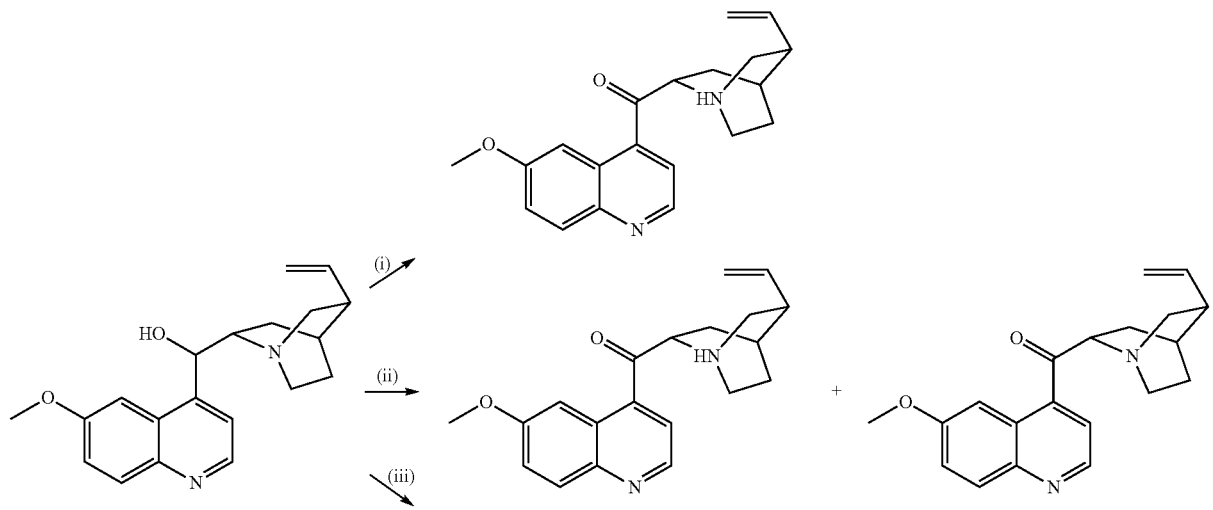

-continued

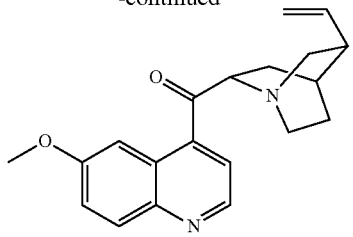

Conditions for Scheme 1: (i) H₂O, acetic acid, anaerobic conditions, 70-80° C., 45 h; (ii) H₂O, acetic acid, O₂, 70-80° C., 45 h; (iii) H₂O, acetic acid, H₂O₂, 70-80° C., 45 h.

In exemplary embodiments, treatment of the compound of Formula III, compound of Formula IV, quinine monomer, quinidine monomer, cinchonine monomer, or cinchonidine monomer with acid and/or heat may be used to improve thermal stability of the monomer.

In exemplary embodiments, wherein the tagging unit is a compound of Formula III, the source of the compound may be a mixture of monomeric and dimeric forms. For example, quinine is known to exist in monomer and dimer forms in chloroform solutions, wherein the dimer of quinine was shown to be a π-π complex with nearly parallel quinoline rings.

In certain embodiments, the tagging unit is quinicine (CAS 84-55-9); quinicine hydrochloride (CAS 52211-63-9); quinicine oxalate; quinicine sulfate; quinicine, tartrate, hexahydrate; cinchonicine (also called cinchotoxine, CAS 69-24-9); quininone (CAS 84-31-1); or cinchoninone (also called cinchonan-9-one, CAS 14509-68-3); quinine (CAS 130-95-0), quinine monohydrochloride dihydrate (CAS 6119-47-7), quinine hemisulfate monohydrate or quinine sulfate (CAS 6119-70-6), quinine bisulfate (CAS 549-56-4), quinidine (56-54-2), cinchonidine (CAS 485-71-2), cinchonine (CAS 118-10-5).

In exemplary embodiments, the scale-inhibiting polymer may include one or more monomers, groups, or units, as necessary or desired, in addition to the scale-inhibiting units and tagging units described herein. For example, scale inhibiting polymer may include one or more other groups resulting from a polymerization initiator or can include end-capping groups. In exemplary embodiments, the end capping groups are derived from initiator compounds used in the polymerization of the monomers.

In exemplary embodiments, the polymerization of the monomers can be carried out in the presence of polymerization initiators including, without limitation, inorganic peroxides, for example ammonium persulfate (APS), hydroxymethanesulfinic acid monosodium salt dehydrate, potassium persulfate, and sodium persulfate; organic peroxides, for example tert-butyl hydroperoxide (TBHP), tert-butyl peracetate, cumene hydroperoxide, 2,5-Di(tert-butylperoxy)-2,5-dimethyl-3-hexyne, dicumyl peroxide, 2,5-bis(tert-butylperoxy)-2,5-dimethylhexane, 2,4-pentanedione peroxide, 1,1-bis(tert-butylperoxy)-3,3,5-trimethylcyclohexane, 1,1-bis(tert-butylperoxy)cyclohexane, 1,1-bis(tert-amylperoxy)cyclohexane, benzoyl peroxide, 2-butanone peroxide, tert-butyl peroxide, lauroyl peroxide, tert-butyl peroxybenzoate, and tert-butylperoxy 2-ethylhexyl carbonate; azo compounds, for example azobisisobutyronitrile (AIBN), 4,4'-azobis(4-cyanovaleric acid), 1,1'-azobis(cyclohexanecarbonitrile), 2,2'-azobis(2-methylpropionamidine) dihydrochloride, and 2,2'-azobis(2-methylpropionitrile); tetrakis(hydroxymethyl)phosphonium sulfate (THPS); cerium ammonium nitrate; perchlorates; triphenylphosphine; and the like, and compositions or mixtures comprising one or more of these initiators. In exemplary embodiments, the initiator is selected from the group consisting of ammonium persulfate, tert-butyl hydroperoxide and 4,4'-azobis(4-cyanovaleric acid).

In exemplary embodiments, the polymerization initiators are generally used in an amount of about 0.01 to about 10 weight percent based on the total weight of the monomers. In exemplary embodiments, the polymerization initiators may be used in conjunction with heat to initiate polymerization of the monomers. In exemplary embodiments, two or more initiators may be used, for example an inorganic peroxide and an organic peroxide. In certain embodiments, APS and an organic peroxide are used to initiate the polymerization. The initiator or initiators used to achieve polymerization may affect the physical properties of the resulting polymer. The initiator or initiators may be added to the polymerization reaction mixture, for example, at the start of the reaction, at various times during the polymerization, and/or gradually over a period of time, e.g. several hours. If two or more initiators are used, the initiators may be dosed simultaneously or sequentially during the polymerization reaction. In exemplary embodiments, one initiator may be dosed at the start of the polymerization reaction, at various times during the polymerization, and/or gradually over a period of time, and a different initiator may be used at later stages of the polymerization reaction.

In exemplary embodiments, the scale-inhibiting polymer may be prepared by any polymerization method. For example, a free-radical polymerization method may be employed. Other exemplary methods include aqueous bulk/dispersion polymerization, solution polymerization, or emulsion polymerization. In an exemplary embodiment, the polymerization process is solution polymerization, wherein water is charged to a reaction vessel fitted with a mechanical stirrer and water condenser and heated to a temperature within a range of 45 to 110° C. One or more polymerization initiators may be added to the reactor. The tagging unit monomer may be added to the reactor, added to the monomer feed or fed separately. A monomer feed(s), soluble initiator feed and optionally a chain transfer reagent feed may be added to the vessel at a predetermined time or over a period of time.

In exemplary embodiments, the scale-inhibiting polymer has a weight average molecular weight of about 500 to about 20,000 Daltons, about 1200 to about 15000 Daltons, about 4000 to about 10000 Daltons, or about 1500 to about 3000 Daltons.

In one embodiment, the scale-inhibiting polymer is a copolymer. In another embodiment, the scale-inhibiting polymer is a terpolymer.

In exemplary embodiments, the scale-inhibiting polymer including the tagging unit(s) can be detected by any method appropriate, such as fluorometry. An exemplary detection method is a fixed wavelength fluorometer. Usually, detection is at the polymer maxima excitation (ex) and emission (em) wavelengths. These can be determined using a scanning fluorometer in scanning mode. It is considered that the level of fluorescence may be determined by the Beer-Lambert Law. For example, polymer concentrations may be assigned by comparison of the emission intensity of the polymer sample with a calibration plot obtained from polymer samples of a known concentration. Any detection methods which utilize the fluorescence properties of the polymer may be used, as necessary or desired.

As referred to herein, the phrase "effective detection amount" means an amount of tagging units sufficient to provide suitable detection in a particular application. In exemplary embodiments, the scale-inhibiting polymer comprises an effective detection amount of tagging units. In exemplary embodiments, the scale-inhibiting polymer contains from about 0.01% to about 30% (by weight) 0.01% to about 10%, about 0.2% to about 10%; about 0.25% to about 10%; about 1% to about 7%; about 2% to about 5%; about 0.01% to about 2% tagging units based on the total units in the polymer. In an exemplary embodiment, the scale inhibiting polymer has less than about 3.7% by weight tagging units, based on the total units in the polymer.

In exemplary embodiments, the thermal stability of the scale-inhibiting polymers can evaluated by heating the polymer in a solvent, for example water or brine, to a temperature, for example about 80° C., about 90° C., about 100° C., about 110° C., about 120° C., or about 130° C., and keeping the polymer in the solvent at that temperature for a period of time, for example about one week.

In exemplary embodiments, the polymer comprises a tagging unit which is a compound of Formula I, II, III, or IV or a salt, hydrate, salt hydrate, stereoisomer, dehydrate or derivative thereof, and the polymer has a thermal stability such that when the polymer is kept at a temperature of about 80° C. in water or brine for about one week, there is less than about 15%, about 10%, about 5%, about 4%, or about 3% decrease in emission intensity. In exemplary embodiments, the polymer comprises a tagging unit which is a compound of Formula I, II, III, or IV or a salt, hydrate, salt hydrate, stereoisomer, dehydrate or derivative thereof, and the polymer has a thermal stability such that when the polymer is kept at a temperature of about 130° C. in water or brine for about one week, there is less than about 20%, about 15%, about 13%, about 10%, about 5%, or about 4% decrease in emission intensity.

In exemplary embodiments, the water is water at about pH 7 or about pH 8. In exemplary embodiments, the brine is natural brine or synthetic brine. In exemplary embodiments, the polymer has a thermal stability such that when the polymer is kept at a temperature of about 80° C. in water for about one week, there is less than about 10%, about 5%, about 4%, or about 3% decrease in emission intensity. In exemplary embodiments, the polymer has a thermal stability such that when the polymer is kept at a temperature of about 130° C. in water for about one week, there is less than about 15%, about 10% or about 5% decrease in emission intensity. In exemplary embodiments, the polymer has a thermal stability such that when the polymer is kept at a temperature of about 130° C. in water at about pH 8 for about one week, there is less than about 15%, about 13%, or about 10% decrease in emission intensity. In exemplary embodiments, the polymer has a thermal stability such that when the polymer is kept at a temperature of about 130° C. in brine for about one week, there is less than about 20%, about 15% or about 10% decrease in emission intensity.

In certain embodiments, the polymer comprises a tagging unit which is a compound of Formula III, or a salt, hydrate, salt hydrate, stereoisomer, dehydrate or derivative thereof is a compound, and has a thermal stability such that when the polymer is kept at a temperature of about 80° C. in water for about one week, there is less than about 4% decrease in emission intensity. In certain embodiments, the polymer comprises a tagging unit which is a compound of Formula I, or a salt, hydrate, salt hydrate, stereoisomer, dehydrate or derivative thereof is a compound, and has a thermal stability such that when the polymer is kept at a temperature of about 130° C. in water for about one week, there is less than about 10% decrease in emission intensity. In certain embodiments, the polymer comprises a tagging unit which is a compound of Formula I, or a salt, hydrate, salt hydrate, stereoisomer, dehydrate or derivative thereof is a compound, and has a thermal stability such that when the polymer is kept at a temperature of about 130° C. in water at about pH 8 for about one week, there is less than about 13% decrease in emission intensity. In certain embodiments, the polymer comprises a tagging unit which is a compound of Formula I, or a salt, hydrate, salt hydrate, stereoisomer, dehydrate or derivative thereof is a compound, and has a thermal stability such that when the polymer is kept at a temperature of about 130° C. in brine for about one week, there is less than about 20% decrease in emission intensity.

In some embodiments, the scale-inhibiting polymer may be included in a scale-inhibiting composition. As referred to herein, the phrase "effective scale-inhibiting amount" means an amount of a scale-inhibiting polymer or a scale-inhibiting composition to provide suitable scale inhibition, removal or reduction. In exemplary embodiments, the scale-inhibiting composition may include an effective scale-inhibiting amount of a scale-inhibiting polymer as described herein. Exemplary scale-inhibiting compositions may, for example, contain from about 5 to about 95% by weight of a scale-inhibiting polymer.

The scale-inhibiting composition may optionally include one or more additional ingredients, as necessary or desired, such as water, salts, oils, surfactants, pH adjusting agents (such as acids, bases and buffers), colorants, flow modifiers, etc. In some embodiments, the scale-inhibiting composition may consist essentially of a tagged scale-inhibiting polymer.

In exemplary embodiments, a scale-inhibiting composition includes the scale-inhibiting polymer and a fluid. Exemplary fluids include fluids included in or intended for industrial water systems or process systems, such as boilers, cooling systems, cooling towers, desalination plants, geothermal power production, irrigation systems, mineral ore extraction systems, paper pulping or manufacturing systems, membrane systems. Other exemplary fluids include fluids for use in the oil industry, such as those for use in the treatment of water injection systems, subsea flow lines, topside production equipment and "down-hole" to control scaling in and around the production well-bore.

In exemplary embodiments, the scale-inhibiting composition includes an aqueous composition or a water-based fluid, for example a seawater-based fluids, but other fluids are not excluded. In other embodiments, the scale-inhibiting composition includes a glycol or glycol ether based solvent.

In exemplary embodiments, the scale-inhibiting composition may include one or more scale-inhibiting polymers. In exemplary embodiments, the scale inhibiting composition may include one or more scale-inhibiting polymers in combination with one or more additional additives or water treatment agents such as, for example: surfactants, such as anionic surfactants (e.g. C10-20 alkyl benzene sulfonates, C10-20 olefin sulfonates, C10-20 alkyl sulfates, C10-20 alkyl 1 to 25 mole ether sulfates, C10-20 paraffin sulfonates, C10-20 soaps, C10-20 alkyl phenol sulfates, sulfosuccinates, sulfosuccinamates, lignin sulfonates, fatty ester sulfonates, C10-20 alkyl phenyl ether sulfates, C10-20 alkyl ethanolamide sulfates, C10-20 alpha sulfo fatty acid salts, C10-20 acyl sarcosinates, isethionates, C10-20 acyl taurides, C10-20 alkyl hydrogen phosphates), non-ionic surfactants (e.g. ethoxylated and/or propoxylated C10-20 alcohols, ethoxylated and/or propoxylated C10-20 carboxylic acids, alkanolamides, amine oxides, and/or C10-20 acyl sorbitan and/or glyceryl ethoxylates) amphoteric surfactants (e.g. betaines, sulfobetaines, and/or quaterised imidazolines), and/or cationic surfactants (e.g. benzalkonium salts, C10-20 alkyl trimethyl ammonium salts, and/or C10-20 alkyl trimethyl); sequestrants, chelating agents, corrosion inhibitors (e.g., imidazoline and quaterantry ammonium salts); and/or other threshold agents (e.g. polymers such as aminometholine phosphonate polymers, polyacrylic acid, or non polymeric agents such as sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid and its salts); tolyltriazole and mixtures of nitrate, benzqate, HHP and/or PTCB); hydrate inhibitors (e.g., methanol); cinetic inhibitors such as anti-agglomeration agents; biocides (e.g. tetrakis (hydroxymethyl) phosphonium salts, formaldehyde, glutaraldehyde, DENPA, bromopol isothiazoronal); oxidising biocides and/or bleaches (e.g. chlorine, chlorine dioxide, hydrogen peroxide, sodium perborate); foam controlling agents such as silicone antifoams; oxygen scavengers such as hydrazines and/or hydroxylamines; pH controlling and/or buffering agents such as amines, borates, citrates and/or acetates; chromium salts; zinc salts; asphaltene inhibitors; wax inhibitors; demulsifiers; other scale inhibitors; and/or other water treatment agents such as polymeric dispersants and coagulants including polymaleic, polyacrylic and polyvinylsulfonic acids and their salts, starches and/or carboxy methyl cellulose, and/or molybdates.

In exemplary embodiments, the scale-inhibiting composition may include from about 5 to about 95% by weight of a tagged scale-inhibiting polymer and from about 5 to about 90% by weight of one or more of any of the aforesaid additives or water treatment agents.

In an exemplary aqueous scale-inhibiting composition, the scale-inhibiting polymer may be combined with the water using any suitable method. For example, the scale-inhibiting polymer may be dissolved, suspended, dispersed or emulsified in the water. The amount of water in the aqueous scale-inhibiting composition may vary, as necessary or desired. For example an aqueous scale-inhibiting composition may comprise about 20% to about 80% scale-inhibiting polymer, based on the total weight of the aqueous scale-inhibiting composition.

In an exemplary embodiment, the pH of the scale-inhibiting composition may be such that the acidic functionalities of the polymer or copolymer are neutralized. For example, the composition may be neutralized by adjusting the pH of the composition to a pH in a range of about 2 to about 13.

The performance or efficacy of scale-inhibiting compositions can be evaluated using any known methods for antiscalant or scale inhibitor performance testing, including but not limited to: static antiprecipitation (jar tests), crystal growth kinetics, rotation tests and dynamic scale inhibition tests, for example dynamic tube blocking test, stirred vessel test, and rotating spindle test.

In an exemplary embodiment, the scale-inhibiting composition is a water treatment solution that comprises a scale-inhibiting polymer including one or more tagging units, and a solvent. According to the embodiments, the scale-inhibiting polymer includes one or more scale-inhibiting units and one or more tagging units as described herein. In a particular embodiment, a water treatment solution for inhibiting scale formation comprises a scale-inhibiting polymer including: scale-inhibiting monomers selected from allylsulfonate salts, maleic acid, and maleic anhydride; and one or more tagging units as described herein.

In one exemplary embodiment, a method for preventing or controlling scale formation in systems comprising fluid circulation comprises the steps of: (a) adding to the system or fluid a predetermined amount of a scale-inhibiting polymer having one or more tagging units and one or more scale-inhibiting units; (b) periodically, continually, or continuously measuring the amount of tagging units in the system or fluid; and (c) periodically, continually, or continuously further adding more tagged scale inhibiting polymer to the system or fluid when the measured amount of tagging units is below a predetermined value.

In exemplary embodiments, the step of adding the scale-inhibiting polymer includes adding a scale-inhibiting composition that comprises the scale-inhibiting polymer. In another exemplary embodiment, adding the scale-inhibiting polymer to the system or fluid to be treated comprises forcing the tagged scale-inhibiting polymer into an oilfield where the fluid will be circulated.

According to the exemplary methods, the scale-inhibiting polymer may be added in any amount to produce a necessary or desired effect in the system or fluid to be treated. For example, an effective scale-inhibiting amount of the polymer may be added to the system or fluid, i.e., an amount capable of reducing or inhibiting the amount of scale in the system by a predetermined amount. According to some embodiments, an effective scale-inhibiting amount is an amount sufficient to inhibit calcium carbonate, calcium sulfate, barium sulfate, and/or calcium phosphate scale formation. Generally, scale formation or deposition occurs when scale-forming ions are above the saturation value of a solution and become thermodynamically unstable with respect to precipitation. Ion clusters begin to form in solution and these clusters eventually attain sufficient density to become physical crystals (also referred to as nucleation). Nucleated crystals grow and aggregate to form larger crystals. Scale formation or deposition may be controlled by utilizing deposition control agents, or threshold inhibitors, that inhibit precipitation at dosages far below stoichiometric level required for sequestration or chelation. These materials affect the kinetics of the nucleation and crystal growth of scale-forming salts, and permit supersaturation without scale formation. The effective scale-inhibiting amount of a scale-inhibiting polymer will generally depend on the particular system to be treated and scale-inhibiting moieties in the scale-inhibiting polymer. For example, the effective scale-inhibiting amount of scale-inhibiting polymer in a particular system to be treated may be influenced by factors such as the area subject to deposition, pH, temperature, water quantity, and the respective concentration in the water of the potential scale and deposit forming species. In various embodiments, an exemplary scale-inhibiting composition will be effective in the system to be treated when the scale-inhibiting polymer is provided at levels less than about 200 parts per million (ppm), less than about 100 ppm, less than about 50 ppm, less than about 35 ppm, less than about 20 ppm, or less than about 10 ppm on the basis of the fluid in the system to be treated. In some embodiments, the scale-inhibitor polymer is effective at concentrations of about 0.5 to about 200 ppm, about 0.5 to about 100 ppm, about 0.5 to about 50 ppm, about 0.5 to about 35 ppm, about 0.5 to about 10 parts ppm, about 0.5 to about 3 parts ppm, about 2 to about 10 ppm, or about 4 to about 7 ppm. The scale-inhibiting polymer or composition can be added directly into the desired aqueous system to be treated in a fixed quantity or can be added continuously or intermittently to the aqueous system as necessary or desired for the system to be treated.

In exemplary embodiments, the step of measuring the amount of tagging units in the system or fluid includes using fluorescent detection to detect the amount of tagging units in the system or fluid. For example, a sample of fluid may be extracted from the system being treated with the scale-inhibiting polymer. The fluorescent intensity of that sample may be determined at one or more wavelengths. A standard calibration curve may be provided to correlate the detected fluorescent intensity of the system or fluid, with a corresponding concentration of scale-inhibiting polymer (or tagging units) in the system or fluid.

In exemplary embodiments, when the measured amount of tagging units (or the scale-inhibiting polymer) in the system or fluid being treated drops below a predetermined value, more scale-inhibiting polymer may be added to the system or fluid. The predetermined value of scale-inhibiting polymer may be any amount necessary or desired for the particular system or fluid being treated. For example, experiments can be conducted in a laboratory to determine an effective minimum inhibitor concentration (MIC) of scale-inhibiting polymer for a particular system or fluid, i.e., that concentration which just inhibits inorganic scale formation under simulated conditions. In an exemplary method, the amount of scale-inhibiting polymer in the system or fluid can be compared to the MIC value to determine when it may be necessary or desirable to reintroduce the polymer to the system or fluid.

A broad variety of aqueous systems may be treated to reduce scale using the methods described herein. Non-limiting examples of such aqueous systems include boiler water, cooling water, seawater (e.g., in oil platform applications), brackish water, oilfield water (e.g., topside and/or downhole), municipal treatment plant water, and industrial treatment plant water. The amount of scale-inhibiting polymer that is effective to reduce or inhibit scale in a particular aqueous system may be determined by routine experimentation in light of the guidance provided herein. The amount of scale-inhibiting polymer added to the aqueous system may vary over a broad range, depending on the nature of the aqueous system and the type of scale. For example, the amount of scale-inhibiting polymer added to the aqueous system may be in the range of about 0.1 part per million to about 50,000 parts per million, by weight based on the capacity of the aqueous system. Various kinds of scale may be treated in accordance with the methods described herein, including without limitation sulfate, carbonate and phosphate salts such as calcium carbonate, calcium sulfate, calcium phosphate, barium sulfate, strontium sulfate, vivianite, and struvite.

By way of example, the scale-inhibiting compositions and methods may be suitably used in systems and fluids such as oilfield injection and production waters, including topside, downhole and rock formation squeeze applications at the well site. In oilfield injection and production waters, scale formation can constrict injection lines, flow lines, and tubing strings. Without being limited by theory, the exemplary scale-inhibiting compositions can modify the crystal growth of nucleating scale particles and interrupting and delaying crystal growth. They also may sequester metal ions, making them unavailable for ion pairing with anions and hence preventing precipitation of insoluble scale.

In one embodiment, the scale-inhibiting polymer or composition may be utilized in a squeeze application. For example, the scale-inhibiting polymer may be diluted in a suitable carrier solvent (usually brine) and propagated out to an optimized radial distance into the oil producing formation, where it is retained and then released slowly back into the aqueous phase during normal well production. In one embodiment, the squeeze process generally includes applying a dilute solution of the scale-inhibiting polymer with surfactant (0.1%) to clean and cool the near wellbore. Once cleaned, a high concentration solution of the scale-inhibiting polymer at between about 5 and about 20% is introduced, followed by a lower concentration solution of the scale-inhibiting polymer. The solutions are left in contact with the reservoir for a period of time effective to allow for adsorption equilibration, after which the well is returned to production. Adhesion to the formation allows the scale-inhibiting polymer to remain within the near-wellbore area and to resist being pumped up in the oil/water emulsion. Although squeeze application of the chemical is the most common method of treating downhole scale, the scale-inhibiting polymer could also be applied by other techniques commonly used offshore, which include gas-lift injection, downhole annulus injection, encapsulation or soluble matrix techniques, sub-sea wellhead injection via umbilical or indeed secondary topside treatments to enhance inhibitor performance as process conditions vary scaling tendency.

In an exemplary embodiment, the scale-inhibiting polymer or composition may be used in a squeeze process wherein after the high concentration solution of the scale-inhibiting polymer or composition is applied, an overflush stage is used to place the solution of scale-inhibiting polymer to the desired depth of a reservoir. In certain embodiments, the reservoir contains a low concentration solution of the scale inhibiting polymer or composition.

One embodiment provides a method for treating scale in a boiler water system, comprising adding an exemplary scale-inhibiting polymer as described herein to boiler water in need of scale treatment, in an effective scale-inhibiting amount to reduce or inhibit scale in the boiler water, as necessary or desired. In one embodiment, the boiler water scale comprises a calcium phosphate.

Another embodiment provides a method for treating scale in a cooling water system, comprising adding an exemplary scale-inhibiting polymer as described herein to cooling water in need of scale treatment, in an effective scale-inhibiting amount to reduce or inhibit scale in the cooling water, as necessary or desired. For example, the scale-inhibiting polymer or composition may be added to the water used in a cooling tower. In an embodiment, the cooling water scale comprises a calcium carbonate.

Another embodiment provides a method for treating scale in a brackish water or seawater system, comprising adding an exemplary scale inhibiting polymer as described herein to at least one of brackish water and seawater in need of scale treatment, in an effective scale-inhibiting amount to reduce or inhibit scale in the brackish water and/or seawater, as necessary or desired. For example, the scale inhibiting polymer or composition may be added to the process water of a desalination plant. In an embodiment, the brackish water and/or seawater scale comprises a calcium carbonate.

Another embodiment provides a method for treating scale in an oilfield water system, comprising adding an exemplary scale inhibiting composition as described herein to oilfield water in need of scale treatment, in an effective scale-inhibiting amount to reduce or inhibit scale in the oilfield water, as necessary or desired. For example, the scale inhibiting polymer or composition may be added to process water on an oil platform. The oilfield water may be down-hole water that is pumped underground (e.g., for enhanced oil recovery) and/or may be used to treat topside oilfield water. In an embodiment, the oilfield water scale comprises a sulfate salt, e.g., barium sulfate and/or strontium sulfate.

Another embodiment provides a method for treating scale in a municipal water treatment system, comprising adding an exemplary scale inhibiting composition as described herein to municipal treatment plant water in need of scale treatment, in an effective scale-inhibiting amount to reduce or inhibit scale in the municipal treatment plant water, as necessary or desired. For example, the scale inhibiting polymer or composition may be added to the process water of a plant that treats water to render it suitable for municipal drinking water, and/or to a plant that treats municipal waste water. In an embodiment, the municipal treatment plant water scale comprises a phosphate, e.g., at least one of struvite and vivianite.

The exemplary scale inhibiting polymers, compositions, and/or methods are contemplated for use in the prevention or inhibition of scale formation in oil or gas applications, for example water injection, production zones, top-side operations, pipelines, and tankage; in pulp or paper applications, for example digestors, headbox, showers and bleach plants; in municipal or industrial applications, for example desalination, cooling towers, sugar refining, and waste treatment; and in metals or mining applications, for example heap leaching, carbon circuits, slurry transport, and digestors. In one embodiment, the scale inhibiting composition is not for use in a reverse osmosis system.

In certain embodiments, the exemplary scale inhibiting polymer, composition, and/or methods are for use in the reduction or inhibition of scale formation associated with biofilms or microbiologically-influenced corrosion, for example manganese related corrosion of stainless steel by manganese depositing biofilms. A biofilm, as referred to herein, is an aggregate of microorganisms in which cells adhere to each other and/or to a surface. The adherent cells are frequently embedded within a self-produced matrix of extracellular polymeric substance (EPS).

The scale-inhibiting polymers, compositions, and/or methods described herein may be used to inhibit or reduce scale formation in any of the foregoing applications.

In another exemplary embodiment, a process for determining a concentration of a scale-inhibiting polymer for inhibiting scale formation comprises introducing an effective scale-inhibiting amount of the scale inhibiting polymer to an aqueous medium; collecting a sample of the aqueous medium; measuring a fluorescence signal of the sample; and determining a concentration of the scale-inhibiting polymer based on the fluorescence signal. According to the embodiments, an effective scale-inhibiting amount is an amount sufficient to inhibit calcium carbonate, calcium sulfate, barium sulfate, and/or calcium phosphate scale formation. According to the embodiments, the scale-inhibiting polymer includes at least one scale-inhibiting unit and one or more tagging units.

Fluorescence Detection

According to the various methods, the fluorescence of a sample containing an exemplary scale-inhibiting polymer with one or more tagging units may be detected using any suitable method. For example, a sample containing the scale-inhibiting polymer may be measured with a fluorometer that excites the sample at a predetermined wavelength, for example, 345 nm or 250 nm, and the emitted signal is collected with a specific wavelength region, for example 410 to 500 nm. In exemplary embodiments, the typical recording region is 300-600 nm.

For a scale-inhibiting polymer containing a quinine (quinine hydrochloride dihydrate) or quinicine tagging unit, the excitation and emission wavelengths for the tagging units are provided in Table 1 below.

TABLE 1

Excitation and emission wavelengths for exemplary tagging units

| Tagging moiety | $\lambda$ max (EX) | $\lambda$ max (EM) | Typical recording region |
|---|---|---|---|
| Quinine (Quinine hydrochloride dihydrate) | 345 nm | 450 nm | 300-600 nm |
| Quinicine | 250 nm | 440 nm | 300-600 |

Because fluorescence is a highly sensitive method, certain samples may require pre-treatment prior to testing. For example, certain samples may require dilution prior to measurement if the fluorescence signal is out of the measurement range of the spectrofluorometer being used.

All constituents of produced water should be considered when determining the proper application of exemplary tagged scale inhibitors described herein, as some of these constituents may also have natural fluorescence properties, for example certain polycyclic hydrocarbons, that may interfere with the detection of the tagging units on the scale-inhibiting polymer. The chemical properties of produced water can vary considerably depending on the location and the geological formation of the oil field as well as the type of hydrocarbons being produced. Produced water properties can also vary throughout the lifetime of a reservoir. Most of the naturally fluorescent properties of produced waters originate from hydrocarbon residues or other production chemicals in the produced waters. Even though the amount of these species might be extremely low, fluorescence can detect these species at very low ppm levels.

In order to minimize any background fluorescence of different produced waters, a pre-cleaning step may be included prior to the measurement of the fluorescence. Pre-cleaning steps prior to the fluorescence measurement can effect of the water quality of the produced water such that the signal sensitivities are similar to those in very pure Milli-Q water. Pre-cleaning steps or methods may include but are not limited to include, for example, cleaning with solid-phase extraction (SPE) cartridges, dialysis techniques, extraction methods for removing hydrocarbons, ultrafiltration methods, membrane centrifugation methods, or other methods used to separate the polymeric species from smaller compounds, for example other treatment chemicals and salts. SPE cartridges are available with variety of stationary phases, each of which can separate analytes according to different chemical properties. In an exemplary pre-cleaning step, one or more SPE cartridges are used to separate a produced water sample into desired and undesired components. Residual nonpolar impurities in the produced water sample may be retained on the C18 stationary phase, while the scale-inhibiting polymer passes through the stationary phase. The scale-inhibiting polymer may be further retained on an anion exchange cartridge for further cleaning treatments. Before the measurement of the tagged scale inhibitor polymer with a fluorometer, the pH may be adjusted, for example to a more acidic pH, to enhance the sensitivity of the fluorescence. When using the C18 cartridges, the pH of the produced water containing the scale inhibitor may be adjusted to obtain full recovery of the scale inhibitor after SPE cartridge cleaning.

Standard calibration curves for different types of waters may have different slopes, which are well in relationship with the sensitivity of the methods. In pure water, there is no interference and no other light-absorbing species and the sensitivity of the method is highest. When measuring the same standards in produced water, the sensitivity can be lower due to the background absorbance or fluorescence. The background absorbance or fluorescence can be reduced minimized with a pre-cleaning step, for example pre-cleaning with a solid-phase extraction (SPE) method. However, because there may be some amount of background absorbance or fluorescence, established a standard calibration curve for the field water is recommended.

Multiple Tagging Use

In exemplary embodiments, the scale-inhibiting polymers can be used in combination or alternation with other tagged polymers, and in particular, with polymers containing fluorescent moieties that have excitation and/or emission that are different from those of the scale-inhibiting polymers described herein. The use of the scale-inhibiting polymers described herein with other tagged polymers would constitute a multi-tagged system. The multi-tagged system could be used, for example, to allow an operator to monitor two different polymers in a system being treated with the exemplary scale-inhibiting polymer. An example of such a system would be when more than one well is drilled and the oil from all wells is collected from one central location. A different scale-inhibiting polymer may be introduced to each well. From a single sample collected at the central location, an operator may determine which specific well requires more scale-inhibiting polymer by monitoring the presence and/or concentration of each tagged polymer.

In instances where the fluorescent tagging moieties are present in sufficiently high concentration, there can be overlap or interference in the fluorescent signals of the different tagging moieties. However, often the squeeze campaigns in the oilfield are done simultaneously to different wells connected to the same wellhead. In exemplary embodiments, the tagged polymers have similar adsorption/desorption profiles. This also means that if the wells are producing equal amounts of water the scale inhibitor levels in each separate well would continue to stay approximately on the same level. In an ideal example, the base polymer is exactly equal having distinguishable tags to enable the detection but also to have very equal scale inhibition performance and adsorption/desorption profile. In exemplary embodiments, the scale inhibitors can be detected in the same water at the level of up to about 40 to about 50 ppm difference in scale inhibitor concentrations. In certain embodiments, the difference of concentration could be as low as about 10 to about 15 ppm level.

In exemplary embodiments, the exemplary scale-inhibiting polymer may be combined in a multi-tagged system with one or more polymers having a different tagging unit than the scale-inhibiting polymer. Exemplary tagging units are described, for example, in one or more of the following references (each of which is incorporated herein by reference in its entirety): U.S. Pat. No. 7,703,516; U.S. Pat. No. 7,943,058; EP 1 636 142; EP 1 639 228; US Pat. Pub. No. US 2012/0032093.

The following examples are presented for illustrative purposes only, and are not intended to be limiting.

EXAMPLES

Example 1. Synthesis and Fluorescence of Exemplary Scale-Inhibiting Polymer Containing Quinine Tags Exemplary scale-inhibiting polymers described in Table 2 below were prepared with varying weight percents of a quinine tagging moiety. Generally, the polymers were prepared by the following steps. First, a reactor was charged with the given amounts of quinine hydrochloride, sodium allyl sulfonate (SAS) and maleic anhydride terpolymer (MA) and EDTA, depending on the weight percent of quinine tagging moiety desired, for example about 131 g of 25 w-% aqueous SAS, about 22 g MA, about 1.8 g of 40 w-% aqueous EDTA and about 0.2-5.9 g quinine hydrochloride (0.3 to 10 w % quinine hydrochloride monomers). The reactor was protected from light. The contents of the reactor were stirred and heated to about 104° C. An initiator solution, containing about 3.8 g ammonium persulfate in about 11 g water, was fed into the reactor over several hours. Once the addition was complete, the system was kept at about 104° C. for 30 minutes. The resulting polymer solution was cooled and pH was set to 6 with potassium hydroxide (45 w-% aqueous).

In Table 2, the data are weight percent of quinine hydrochloride dihydrate, weight average molecular weight (Mw) and weight percent of residual monomers or their reaction products.

TABLE 2

| Sample | Quinine (w-% of monomers) | Mw (Da) | Sodium allyl sulfonate residue (w-%) | Maleic acid residue (w-%) | Fumaric acid residue (w-%) | Quinine residue (w-%) |
| --- | --- | --- | --- | --- | --- | --- |
| 1 | 0.3 | 2300 | 0.04 | 0.002 | 0.09 | 0.002 |
| 2 | 0.5 | 2300 | 0.04 | 0.002 | 0.1 | 0.003 |
| 3 | 1 | 2750 | 0.04 | 0.01 | 0.13 | 0.001 |
| 4 | 2.5 | 2200 | 0.12 | 0.05 | 0.18 | 0.002 |
| 5 | 3.7 | 2100 | 0.24 | 0.16 | 0.33 | 0.01 |
| 6 | 5 | 2000 | 0.45 | 0.38 | 0.41 | 0.02 |
| 7 | 10 | 1700 | 1.6 | 1.4 | 0.56 | 0.13 |

Figure 2:
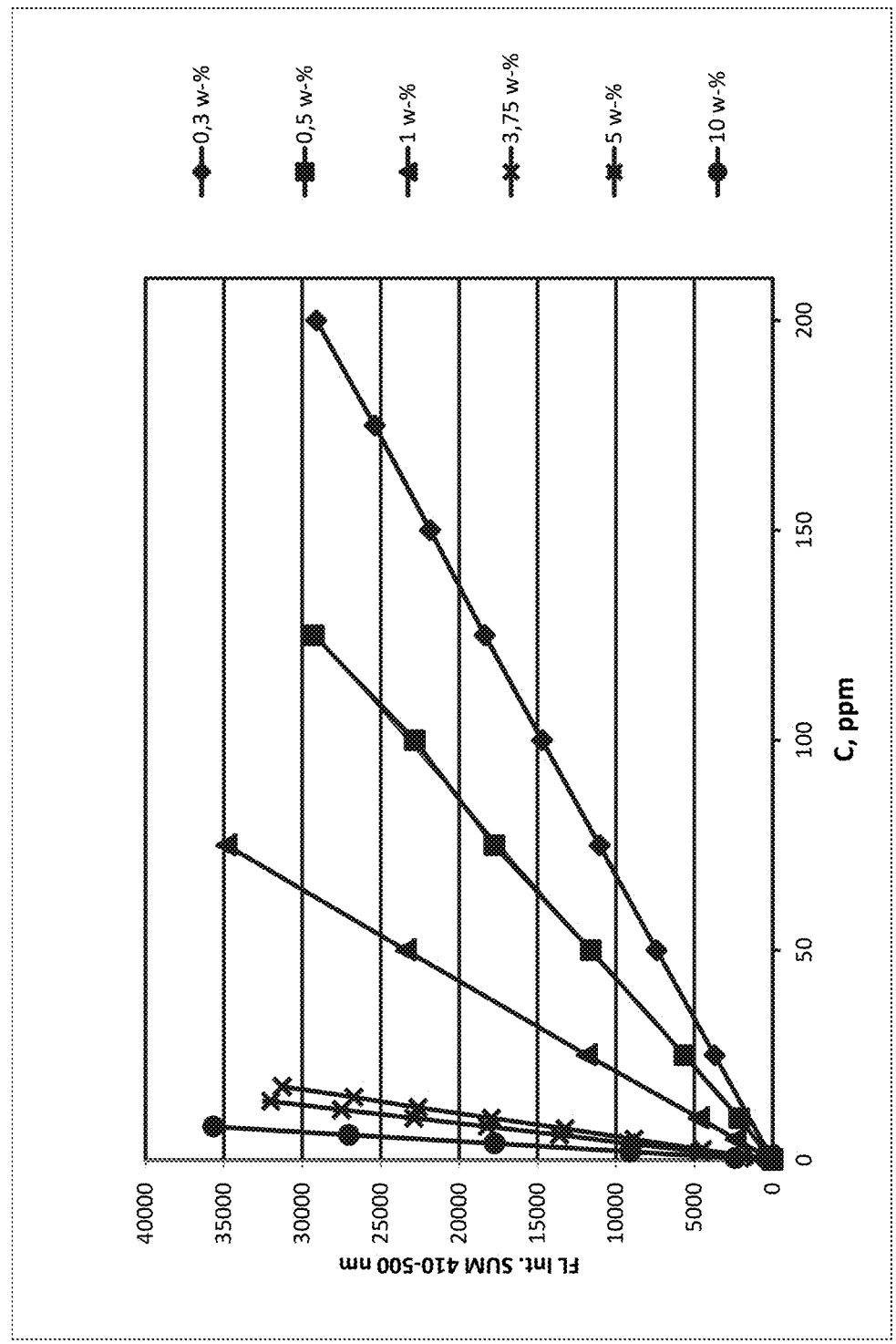
FIG. 2 shows the calibration curves of an exemplary quinine-tagged polymers at various incorporation levels.

The level of the incorporation of the quinine tag was carried out at seven different levels: 0.3 w-%, 0.5 w-%, 1.0 w-%, 2.5 w-%, 3.7 w-%, 5.0 w-%, and 10 w-%. Fluorescence sensitivity was measured for each sample. At 1.0 w-% incorporation level of the quinine to the polymer backbone, low level fluorescence sensitivity was achieved. Notably, quinine fluorescence sensitivity was further enhanced by adjusting the pH, for example with sulfuric acid. In particular, it was observed that, compared to neutral pH, quinine fluorescence is five times better at a pH of about 1. Fluorescence spectra for the quinine-tagged polymers described above, as measured in acidic media at different concentration levels is shown in FIG. 1. The corresponding calibration curve is shown in FIG. 2.

Antiscaling performance of the polymer samples was acceptable and was generally comparable to the untagged polymer, even in severe barium or sulfate scaling conditions.

Figure 3:
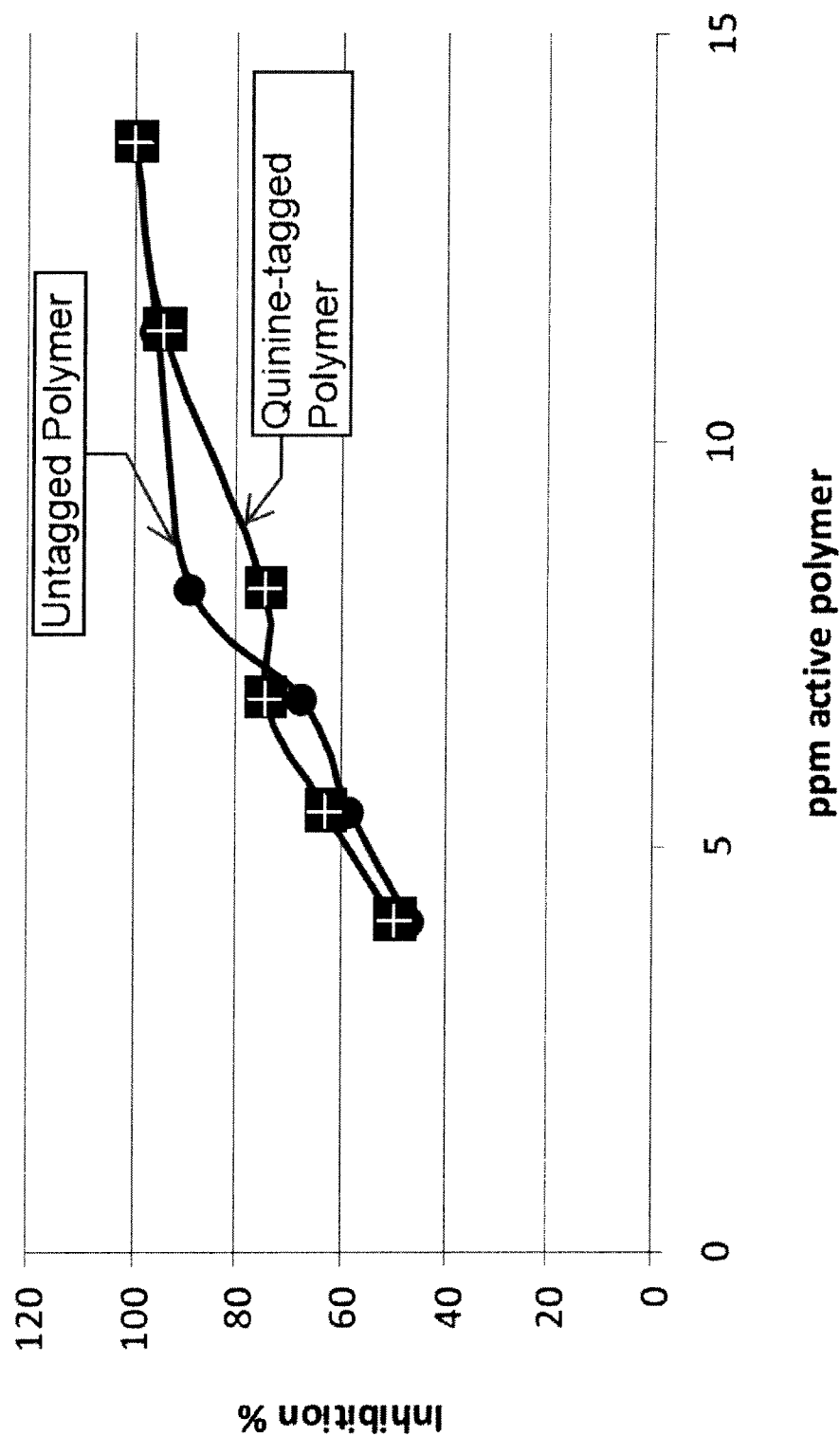
FIG. 3 is a graph of the percent inhibition of an exemplary quinine-tagged polymer and other polymers in severe barium sulfate scaling conditions.

A comparison of the scale-inhibiting activity of the quinine tagged polymer and a commercially available, untagged scale-inhibiting polymer is shown in FIG. 3.

The thermal stability of the polymer samples was evaluated. A sample of the 1.0 w-% quinine tagged polymer was diluted to ¼ with synthetic brine and kept in at 80° C. in a heating chamber for one week. Fluorescence intensities were measured five times during the week (wavelength used was 346 nm). No change to fluorescence intensity was observed during the test period.

Example 2. Quantification of Fluorescence for an Exemplary Tagged Scale-inhibiting Polymer in Produced Water Exemplary quinine tagged scale-inhibiting polymers were tested in produced water from an oilfield. The produced water samples were dosed with the scale-inhibiting polymer at four different concentrations: 0 ppm, 25 ppm, 50 ppm, and 75 ppm. C18 cartridges from Waters were used to pre-clean the produced water samples. The recovery of the tagged polymer was evaluated after the pre-cleaning step.

Figure 4:
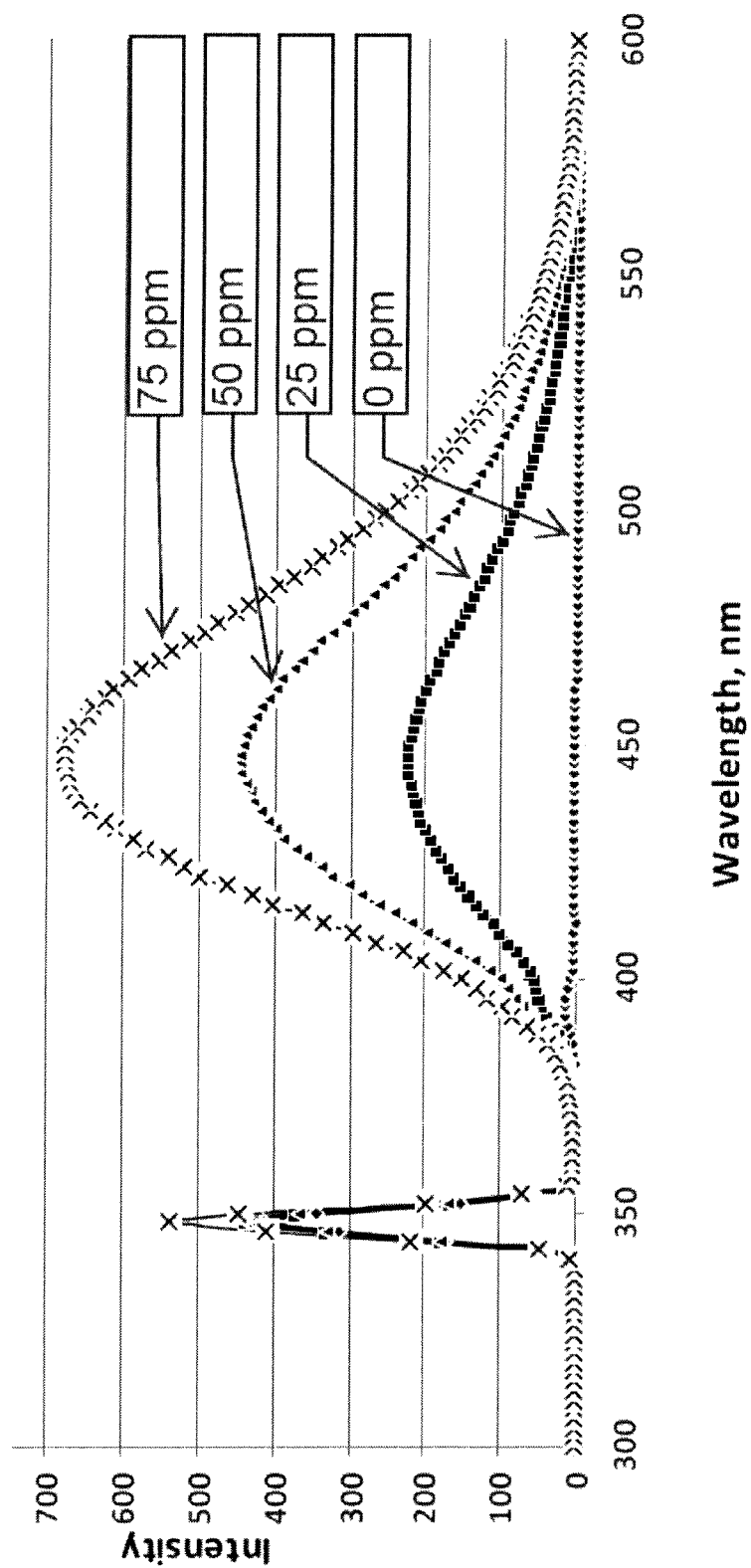
FIG. 4 shows the fluorescence spectra of a quinine-tagged polymer measured in oilfield produced water.

Pre-cleaned samples of the produced water were placed in a 10 mm cuvette and measured with a fluorometer. The samples were excited to 345 nm, and the emitted signal was collected at 410-500 nm. Because fluorescence is a highly sensitive method, certain samples required dilution prior to the measurement if the fluorescence signal was out of the measurement range of the spectrofluorometer being used. Fluorescence signals were calculated together from the selected wavelength region and the sum of intensities, compared to the calibration curve made with the standards in the sample matrix (see FIG. 4).

Example 3. Synthesis and Fluorescence of Exemplary Scale-Inhibiting Polymers Containing Quinicine Tags Quinicine (also called quinotoxine) was prepared by heating quinine or quinine hydrochloride dihydrate (MW 396.92) in aqueous acetic acid with varying solid contents from about 6 to about 50 wt % at 103° C. for about 24 hours. The resulting quinicine (MW=324.42) was used in to prepare the exemplary polymers described below.

Exemplary scale-inhibiting polymers described in Table 3 below were prepared with varying weight percents of a quinicine tagging moiety. Generally, the polymers were prepared by the following steps. First, a reactor was charged with the given amounts of quinicine, sodium allyl sulfonate (SAS) and maleic anhydride terpolymer (MA) and EDTA, depending on the weight percent of quinicine tagging moiety desired, for example about 110 g of 25 w-% aqueous SAS, about 18 g MA, about 1.5 g of 40 w-% aqueous EDTA and about 0.1 to about 0.5 g quinicine (about 0.2 to 0.8 w % quinicine monomers). The reactor was protected from light. The contents of the reactor were stirred and heated to about 104° C. An initiator solution, containing about 3.2 g ammonium persulfate in about 9 g water, was fed into the reactor over several hours. Once the addition was complete, the system was kept at about 104° C. for 30 minutes. The resulting polymer solution was cooled and pH was set to 6 with potassium hydroxide (45 w-% aqueous).

In Table 3, the data are weight percent of quinicine monomer, weight average molecular weight (Mw) and weight percent of residual monomers or their reaction products.

TABLE 3

| Sample | Quinicine target (w-% of monomers) | Mw (Da) | PDI (Mw/Mn) | Sodium allyl sulfonate residue (w-%) | Maleic acid residue (w-%) | Fumaric acid residue (w-%) | Quinicine residue (w-%) |
|---|---|---|---|---|---|---|---|
| 8 | 0.8 | 2300 | 1.7 | 0.057 | 0.017 | 0.127 | 0.006 |
| 9 | 0.4 | 2100 | 1.6 | 0.05 | 0.035 | 0.079 | 0.0014 |
| 10 | 0.2 | 2200 | 1.6 | 0.03 | 0.033 | 0.056 | ND |

Figure 5:
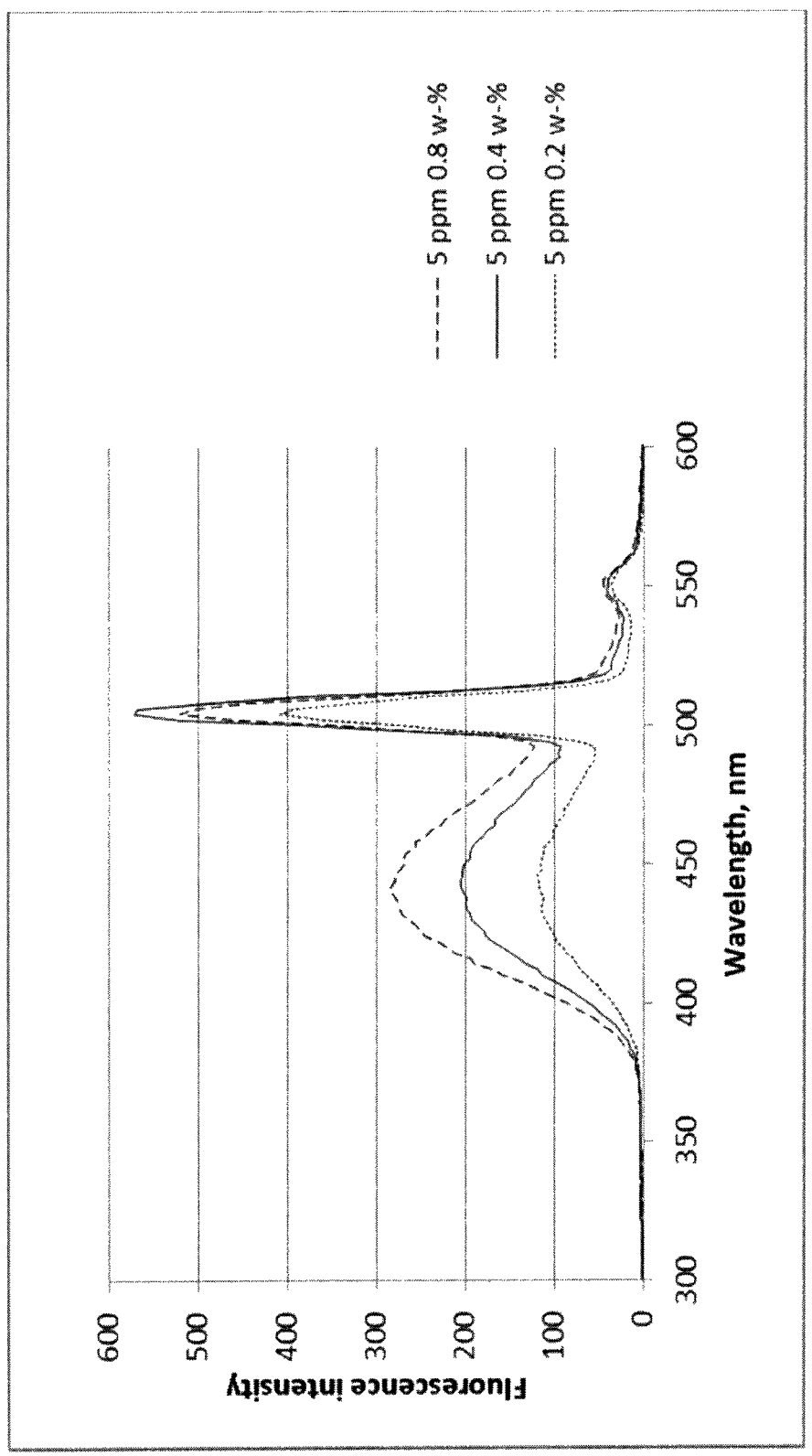
FIG. 5 shows fluorescence spectra of several exemplary quinicine-tagged polymers at various incorporation levels and polymer concentration levels (measured in acidic media).
Figure 6:
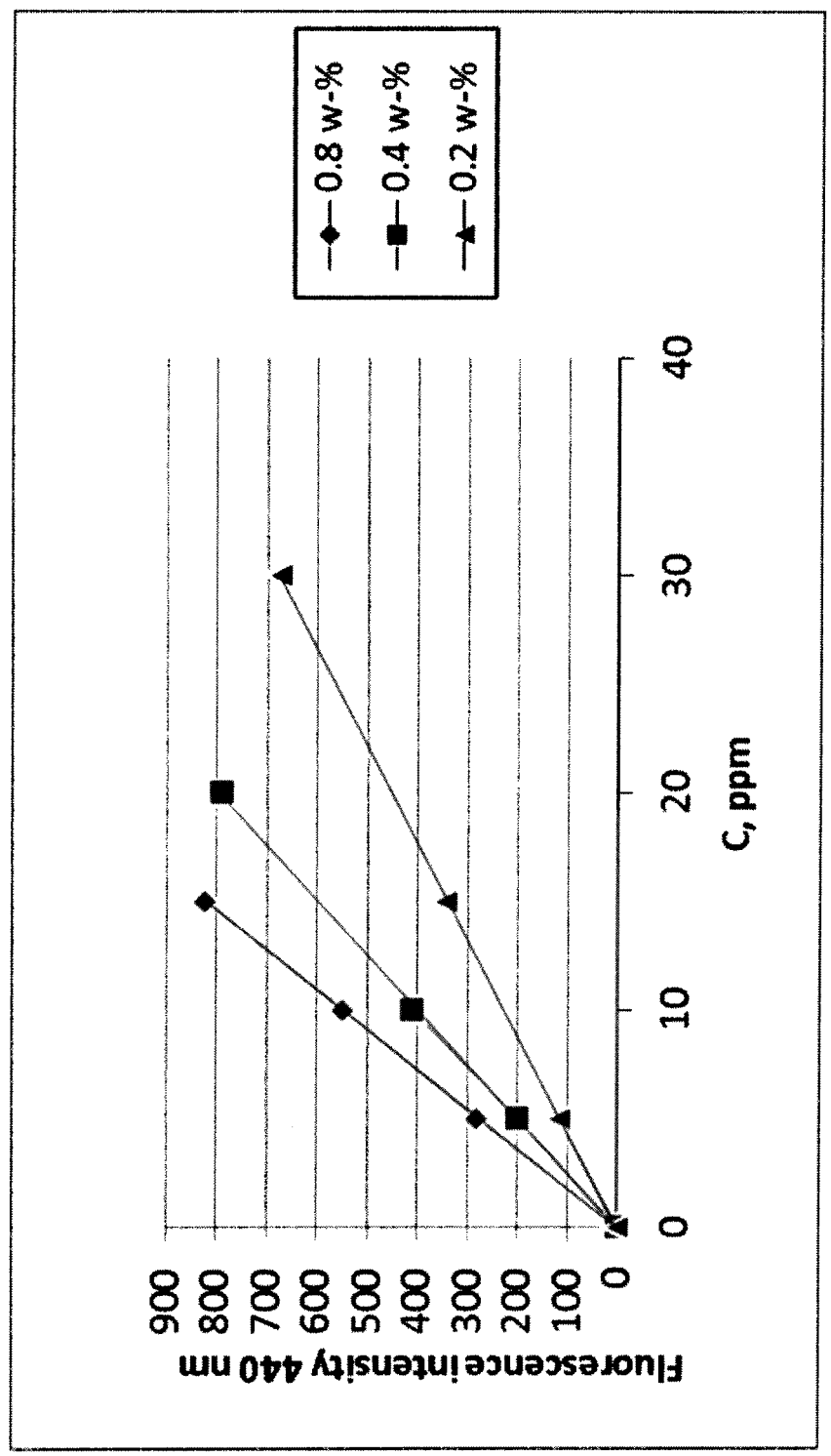
FIG. 6 shows the calibration curves of an exemplary quinicine-tagged polymers at various incorporation levels.

The level of the incorporation of the quinicine tag was carried out at three different levels: 0.2 w-%, 0.4 w-%, and 0.8 w-%. Fluorescence sensitivity was measured for each sample. Low level fluorescence sensitivity was achieved with as low as 0.2 w-% quinicine incorporation. Fluorescence spectra for the quinicine-tagged polymers as described above, as measured in acidic media at different concentration levels, is shown in FIG. 5. The corresponding calibration curve is shown in FIG. 6.

Figure 7:
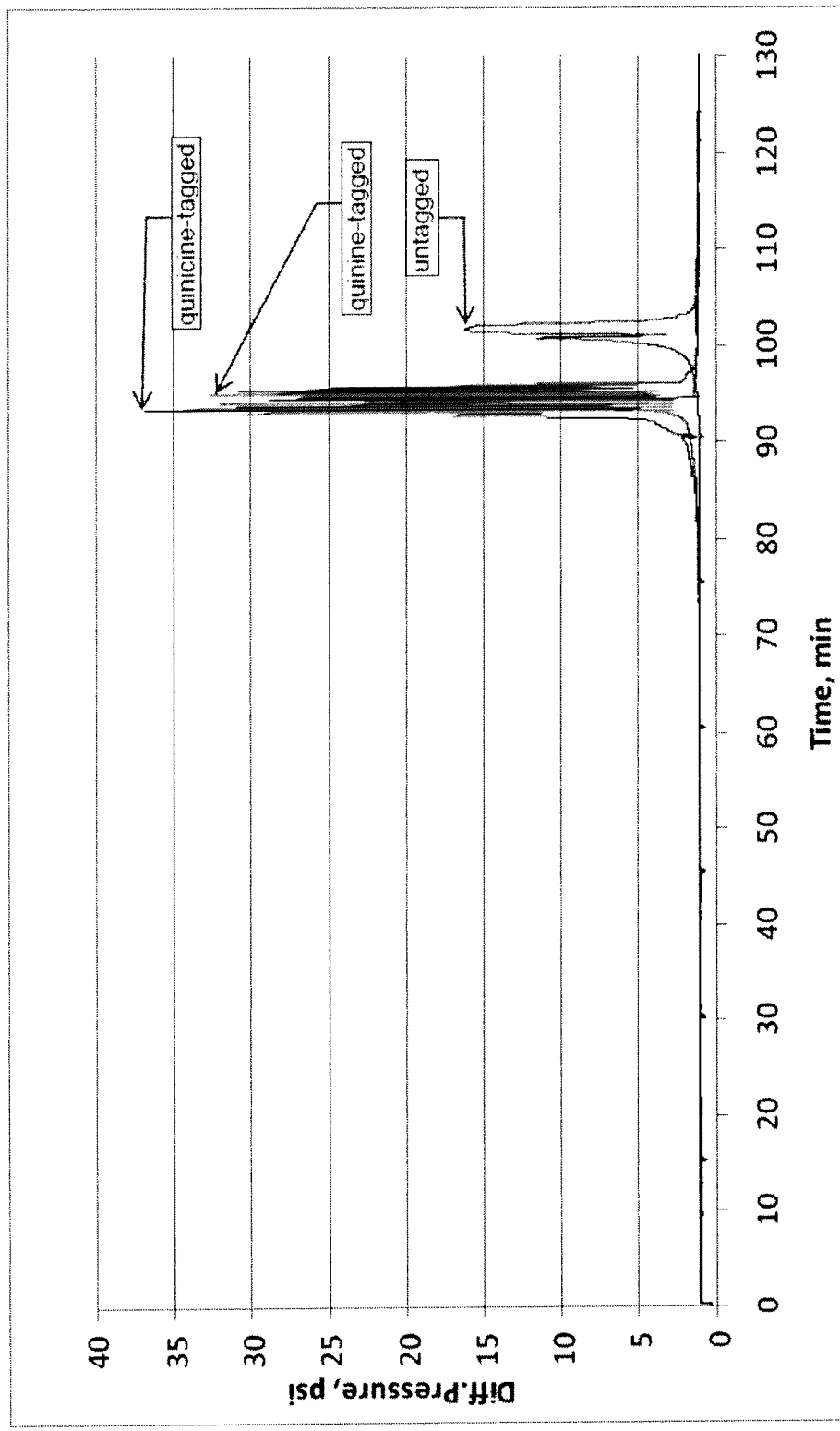
FIG. 7 shows the results of a dynamic scale test (PMAC) for a commercially available scale-inhibiting polymer and two exemplary tagged polymers.

Antiscaling performance of the polymer samples was acceptable and was generally comparable to the untagged polymer or to quinine-tagged polymers, even in severe barium or sulfate scaling conditions. Scale inhibition properties were measured at 70° C. with dynamic scale test method, PMAC, for evaluation of inhibitor performance. The tests were performed at 70° C. with a flow rate of 5 mL/min. $Ba^{2+}$ content in scaling solution was 185 ppm (as BaCl) and $SO_4^{2-}$ concentration was 270 ppm (as $Na_2SO_4$). Inhibitor concentration was decreased gradually until the scaling occurs and ins monitored as increase in differential pressure. A comparison of the scale-inhibiting activity of an exemplary quinicine-tagged polymer, an exemplary quinine-tagged polymer, and a commercially available scale-inhibiting polymer is shown in FIG. 7.

The thermal stability of the polymer samples was evaluated. A sample of the 0.8 w-% quinicine tagged polymer was diluted to ⅓ with synthetic brine and kept at 130° C. in a heating chamber for several days. Fluorescence intensities were measured (wavelength used was 440 nm). No substantial change to fluorescence intensity was observed during the test period.

Figure 8:
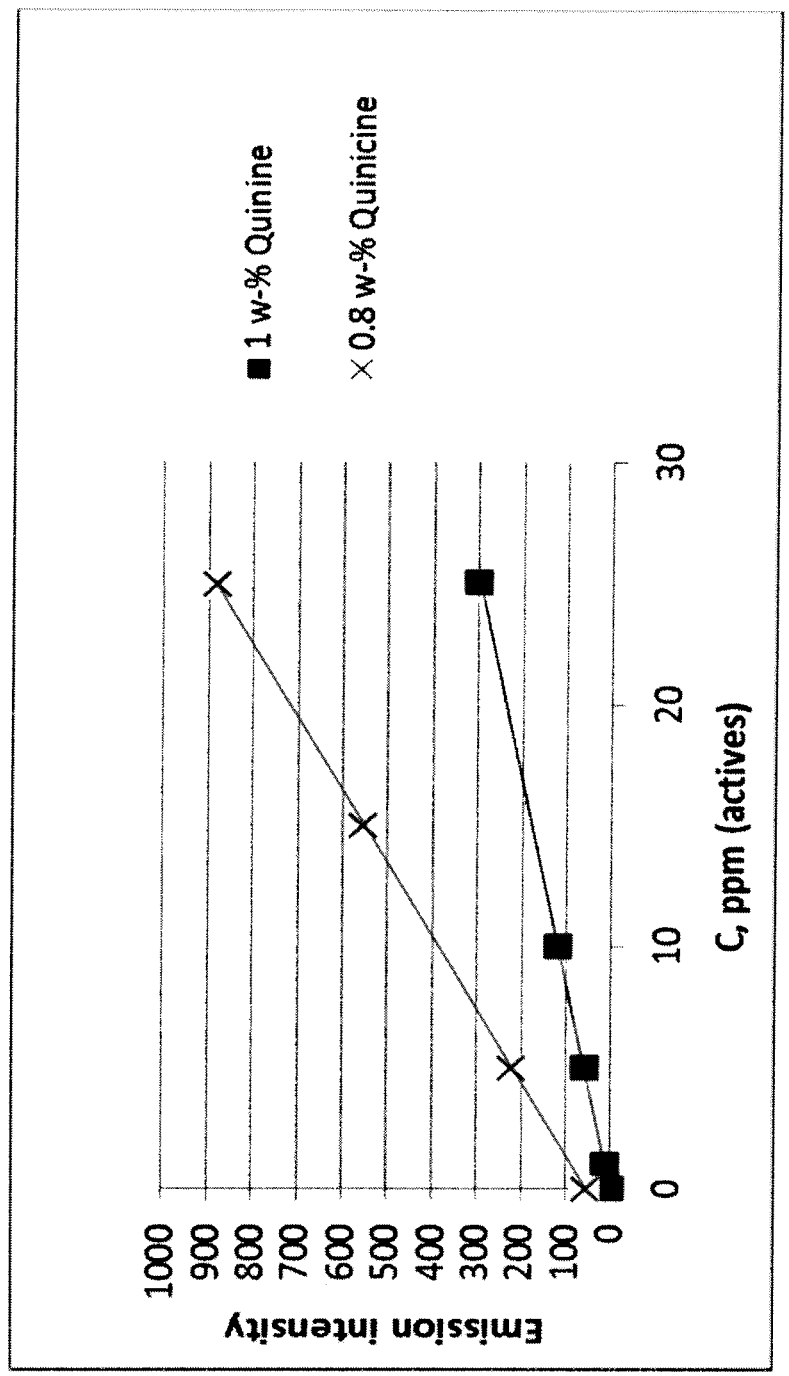
FIG. 8 is a graph illustrating the fluorescent yield of exemplary quinine- and quinicine-tagged polymers.
Figure 9:
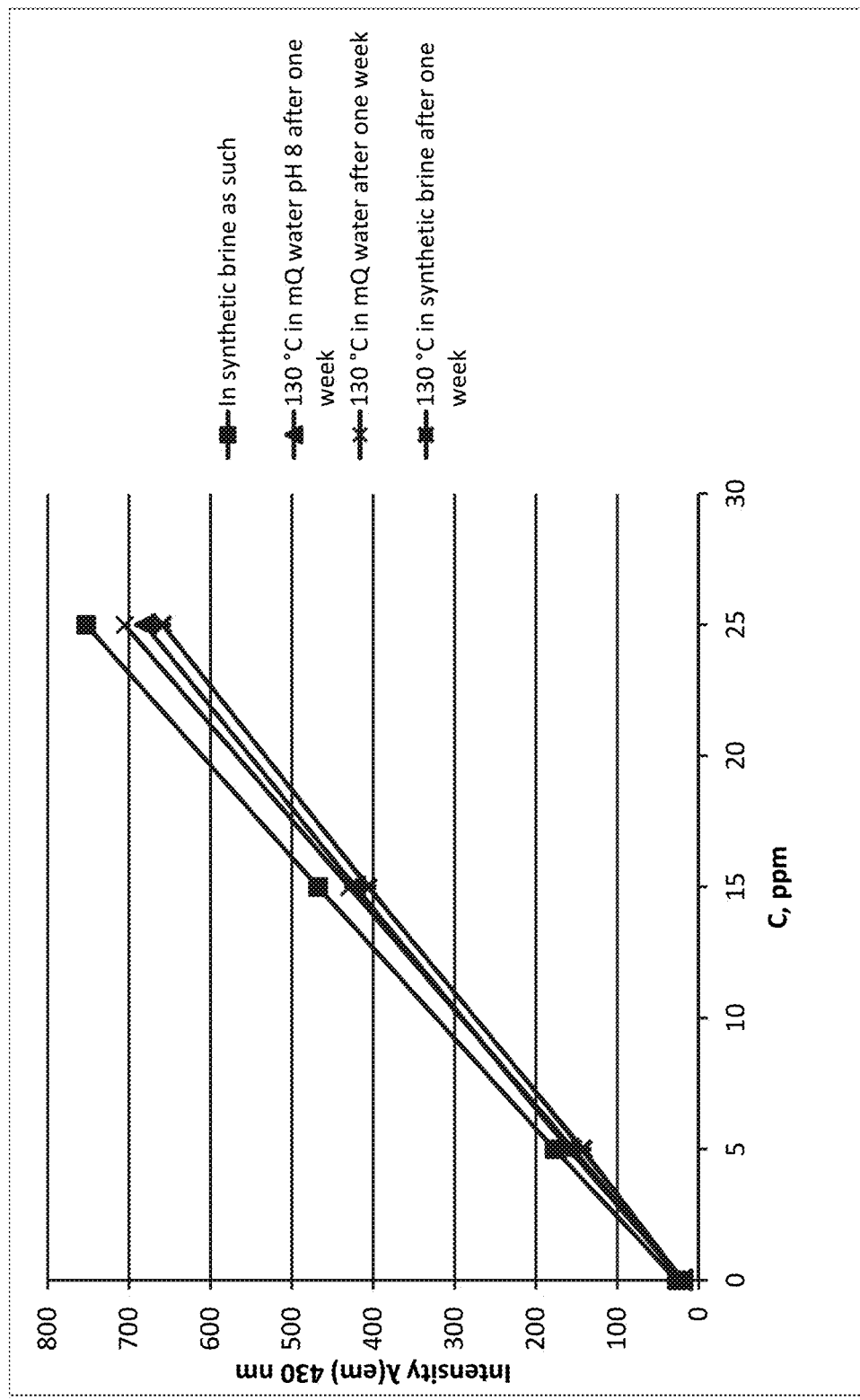
FIG. 9 is a graph illustrating the fluorescent yield of an exemplary quinicine-tagged polymer under varying thermal, pH and salinity conditions.
Figure 10:
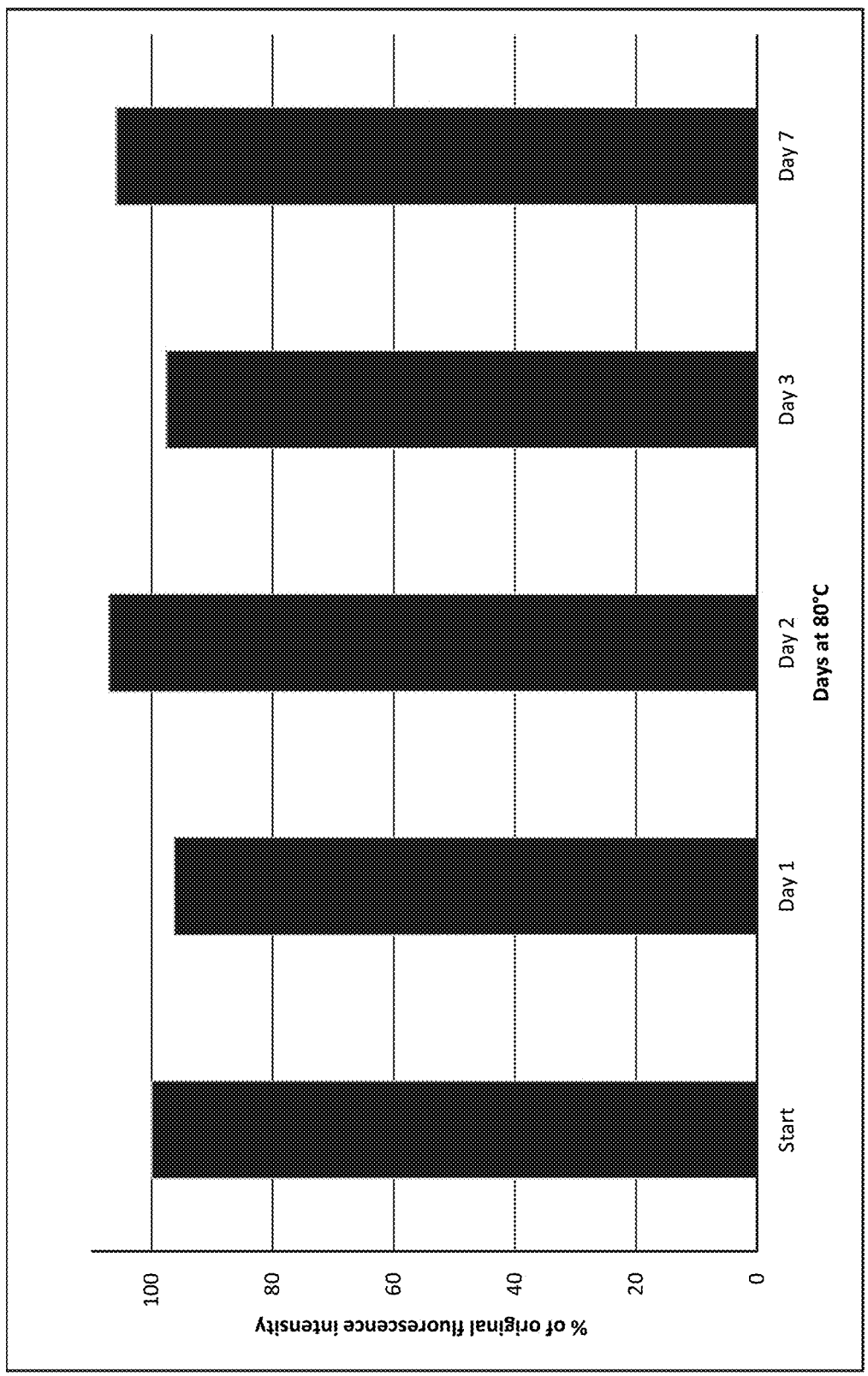
FIG. 10 is a graph illustrating the fluorescent yield of an exemplary quinine-tagged polymer under varying thermal conditions.

The emission intensity for exemplary quinine- and quinicine-tagged polymers is shown in FIG. 8. The thermal stability of an exemplary quinicine-tagged polymer at 130° C. under varying pH and salinity conditions, as quantified by emission intensity, is shown in FIG. 9. The thermal stability of an exemplary quinine-tagged polymer at 80° C., as quantified by emission intensity, is shown in FIG. 10.

We claim:

1. A scale-inhibiting polymer comprising one or more scale-inhibiting units and one or more tagging units, wherein each tagging unit is formed from a compound of Formula I or II:

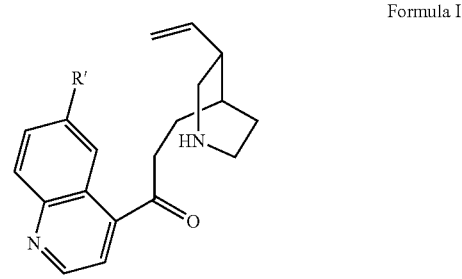

Formula I

-continued

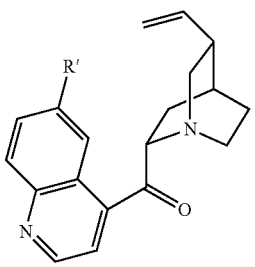

Formula II wherein each R' is independently R, OR, NRC(S)NR$_2$, or NRC(O)NR$_2$;

each R is independently H, C$_1$-C$_6$ alkyl, C$_2$-C$_6$ alkenyl, C$_6$-C$_{14}$ aryl, or C$_7$-C$_{20}$ aralkyl;

and wherein each alkyl or aryl group may be optionally independently substituted with one or more halo, C$_1$-C$_6$ alkyl, or C$_1$-C$_6$ haloalkyl substituents; or a salt, hydrate, salt hydrate, stereoisomer, dehydrate or derivative thereof;

wherein the tagging unit is formed from a compound selected from the group consisting of: a hydrochloride, dihydrochloride, sulfate, bisulfate, or gluconate salt of a compound of Formula I or II, and a hydrate thereof; or wherein the one or more scale-inhibiting units comprises maleic acid or maleic anhydride and sodium allyl sulfonate.

2. The polymer of claim 1, comprising two or more scale-inhibiting units and one or more tagging units.

3. The polymer of claim 1, wherein R' is H.

4. The polymer of claim 1, wherein R' is O(C$_1$-C$_6$ alkyl).

5. The polymer of claim 1, wherein R' is OCH$_3$.

6. The polymer of claim 1, wherein the tagging unit is formed from a compound selected from the group consisting of: a hydrochloride, dihydrochloride, sulfate, bisulfate, or gluconate salt of a compound of Formula I or II, and a hydrate thereof.

7. The polymer of claim 1, wherein the one or more scale-inhibiting units comprises maleic acid or maleic anhydride and sodium allyl sulfonate.

8. The polymer of claim 1, wherein the tagging unit is a quinicine monomer:

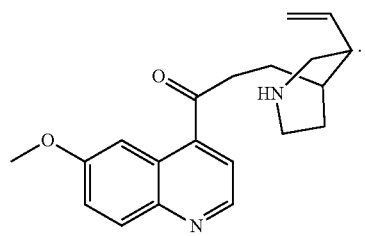 [SMILES: C=CC1CNCCC1CCC(=O)c1ccnc2ccc(OC)cc12 ; "."]

9. The polymer of claim 1, wherein the tagging unit is a chinconicine monomer:

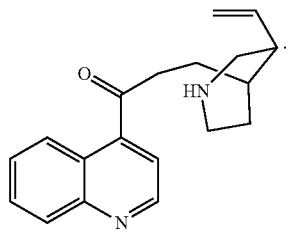 [SMILES: C=CC1CNCCC1CCC(=O)c1ccnc2ccccc12 ; "."]

10. The polymer of claim 1, wherein the tagging unit is a quininone monomer:

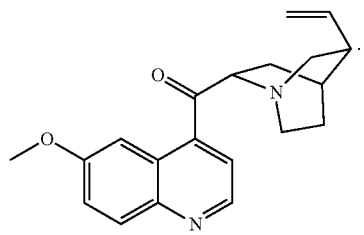 [SMILES: C=CC1CN2CCC1CC2C(=O)c1ccnc2ccc(OC)cc12 ; "."]

11. The polymer of claim 1, wherein the tagging unit is a cinchoninone monomer:

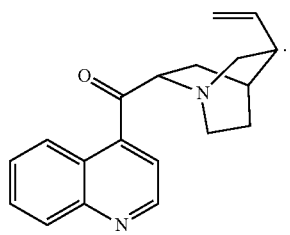 [SMILES: C=CC1CN2CCC1CC2C(=O)c1ccnc2ccccc12 ; "."]

12. The polymer of claim 1, wherein the one or more tagging units is at a weight percent of total monomers of about 0.01% to about 20%.

13. A process for determining a concentration of a scale-inhibiting polymer for inhibiting scale formation, the process comprising:
 (a) introducing an effective scale-inhibiting amount of the scale-inhibiting polymer to an aqueous medium to inhibit calcium carbonate, calcium sulfate, barium sulfate, and/or calcium phosphate scale formation;
 (b) measuring a fluorescence signal of the scale-inhibiting polymer in the aqueous medium; and
 (c) determining a concentration of the scale-inhibiting polymer based on the fluorescence signal;
wherein the scale-inhibiting polymer comprising one or more scale-inhibiting units and one or more tagging units, wherein each tagging unit is formed from a compound of Formula I or II:

Formula I

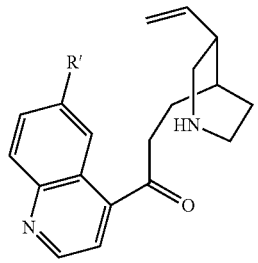

-continued

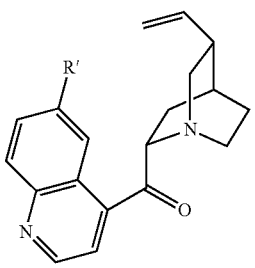

Formula II wherein each R' is independently R, OR, NRC(S)NR$_2$, or NRC(O)NR$_2$;

each R is independently H, C$_1$-C$_6$ alkyl, C$_2$-C$_6$ alkenyl, C$_6$-C$_{14}$ aryl, or C$_7$-C$_{20}$ aralkyl;

and wherein each alkyl or aryl group may be optionally independently substituted with one or more halo, C$_1$-C$_6$ alkyl, or C$_1$-C$_6$ haloalkyl substituents; or a salt, hydrate, salt hydrate, stereoisomer, dehydrate or derivative thereof.

14. A scale-inhibiting composition comprising the scale-inhibiting polymer of claim 1 and a solvent.

15. The composition of claim 14, further comprising at least one additional tagged polymer having an fluorescence emission signal different from that of the scale-inhibiting polymer.

16. A method for preventing or controlling scale formation in systems comprising fluid circulation, which comprising the steps of:

(a) adding to the system or fluid an effective scale-inhibiting amount of a scale-inhibiting polymer;

(b) periodically, continually, or continuously measuring the amount of tagging units in the system or fluid; and (c) periodically, continually, or continuously further adding more scale-inhibiting polymer to the system or fluid when the measured amount of tagging units determined by step (b) is below a predetermined value;

wherein the scale-inhibiting polymer comprising one or more scale-inhibiting units and one or more tagging units, wherein each tagging unit is formed from a compound of Formula I or II:

Formula I

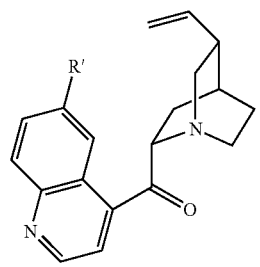

Formula II wherein each R' is independently R, OR, NRC(S)NR$_2$, or NRC(O)NR$_2$;

each R is independently H, C$_1$-C$_6$ alkyl, C$_2$-C$_6$ alkenyl, C$_6$-C$_{14}$ aryl, or C$_7$-C$_{20}$ aralkyl;

and wherein each alkyl or aryl group may be optionally independently substituted with one or more halo, C$_1$-C$_6$ alkyl, or C$_1$-C$_6$ haloalkyl substituents; or a salt, hydrate, salt hydrate, stereoisomer, dehydrate or derivative thereof.

17. The method of claim 16, wherein the amount of scale-inhibiting polymer in the system or fluid is less than 35 parts per million.

18. The method of claim 16, wherein the amount of scale-inhibiting polymer in the system or fluid is less than 0.5 to 35 parts per million.

19. The scale-inhibiting polymer of claim 1, wherein the polymer has a thermal stability such that when the polymer is kept at a temperature of about 130° C. in water for about one week, there is less than about 10% decrease in emission intensity.

20. The process of claim 13, wherein scale-inhibiting polymer comprises two or more scale-inhibiting units and one or more tagging units.

21. The process of claim 13, wherein R' is H.

22. The process of claim 13, wherein R' is O(C$_1$-C$_6$ alkyl).

23. The process of claim 13, wherein R' is OCH$_3$.

24. The process of claim 13, wherein the tagging unit is formed from a compound selected from the group consisting of: a hydrochloride, dihydrochloride, sulfate, bisulfate, or gluconate salt of a compound of Formula I or II, and a hydrate thereof.

25. The process of claim 13, wherein the one or more scale-inhibiting units comprises maleic acid or maleic anhydride and sodium allyl sulfonate.

26. The process of claim 13, wherein the tagging unit is a quinicine monomer:

27. The process of claim 13, wherein the tagging unit is a chinconicine monomer:

28. The process of claim 13, wherein the tagging unit is a quininone monomer:

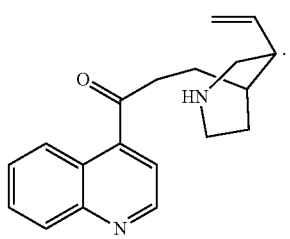 [SMILES: C=CC1CNCCC1CCC(=O)c1ccnc2ccccc12 ; "."]

29. The process of claim 13, wherein the tagging unit is a cinchoninone monomer:

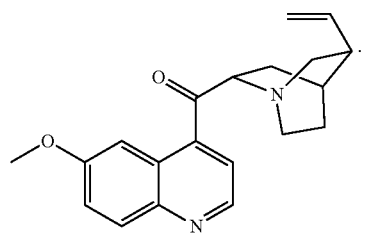 [SMILES: C=CC1CN2CCC1CC2C(=O)c1ccnc2ccc(OC)cc12 ; "."]

30. The process of claim 13, wherein the one or more tagging units is at a weight percent of total monomers of about 0.01% to about 20%.

31. The scale-inhibiting composition of claim 14, wherein scale-inhibiting polymer comprises two or more scale-inhibiting units and one or more tagging units.

32. The scale-inhibiting composition of claim 14, wherein R' is H.

33. The scale-inhibiting composition of claim 14, wherein R' is $O(C_1-C_6$ alkyl).

34. The scale-inhibiting composition of claim 14, wherein R' is $OCH_3$.

35. The scale-inhibiting composition of claim 14, wherein the tagging unit is formed from a compound selected from the group consisting of: a hydrochloride, dihydrochloride, sulfate, bisulfate, or gluconate salt of a compound of Formula I or II, and a hydrate thereof.

36. The scale-inhibiting composition of claim 14, wherein the one or more scale-inhibiting units comprises maleic acid or maleic anhydride and sodium allyl sulfonate.

37. The scale-inhibiting composition of claim 14, wherein the tagging unit is a quinicine monomer:

38. The scale-inhibiting composition of claim 14, wherein the tagging unit is a chinconicine monomer:

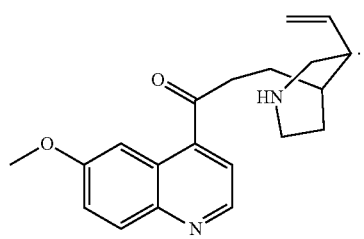 [SMILES: C=CC1CNCCC1CCC(=O)c1ccnc2ccc(OC)cc12 ; "."]

39. The scale-inhibiting composition of claim 14, wherein the tagging unit is a quininone monomer:

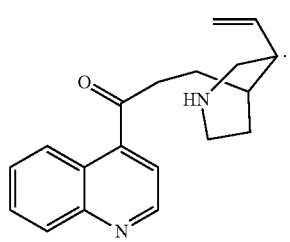 [SMILES: C=CC1CNCCC1CCC(=O)c1ccnc2ccccc12 ; "."]

40. The scale-inhibiting composition of claim 14, wherein the tagging unit is a cinchoninone monomer:

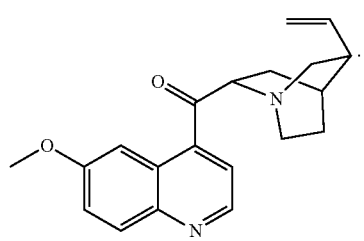 [SMILES: C=CC1CN2CCC1CC2C(=O)c1ccnc2ccc(OC)cc12 ; "."]

41. The scale-inhibiting composition of claim 14, wherein the one or more tagging units is at a weight percent of total monomers of about 0.01% to about 20%.

42. The method of claim 16, wherein scale-inhibiting polymer comprises two or more scale-inhibiting units and one or more tagging units.

43. The method of claim 16, wherein R' is H.
44. The method of claim 16, wherein R' is $O(C_1-C_6$ alkyl).
45. The method of claim 16, wherein R' is $OCH_3$.
46. The method of claim 16, wherein the tagging unit is formed from a compound selected from the group consisting of: a hydrochloride, dihydrochloride, sulfate, bisulfate, or gluconate salt of a compound of Formula I or II, and a hydrate thereof.

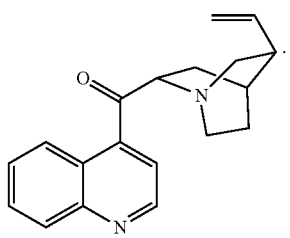 [SMILES: C=CC1CN2CCC1CC2C(=O)c1ccnc2ccccc12 ; "."]
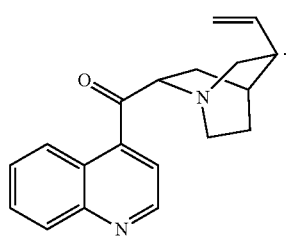

47. The method of claim 16, wherein the one or more scale-inhibiting units comprises maleic acid or maleic anhydride and sodium allyl sulfonate.

48. The method of claim 16, wherein the tagging unit is a quinicine monomer:

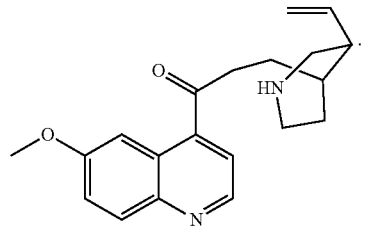 [SMILES: C=CC1CNCCC1CCC(=O)c1ccnc2ccc(OC)cc12 ; "."]

49. The method of claim 16, wherein the tagging unit is a chinconicine monomer:

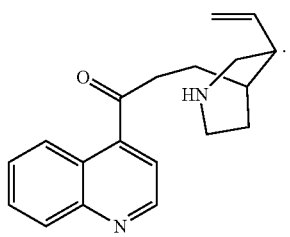 [SMILES: C=CC1CNCCC1CCC(=O)c1ccnc2ccccc12 ; "."]

50. The method of claim 16, wherein the tagging unit is a quininone monomer:

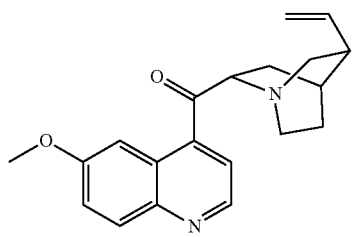

51. The method of claim 16, wherein the tagging unit is a cinchoninone monomer:

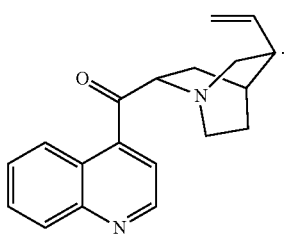 [SMILES: C=CC1CN2CCC1CC2C(=O)c1ccnc2ccccc12 ; "."]

52. The method of claim 16, wherein the one or more tagging units is at a weight percent of total monomers of about 0.01% to about 20%.

* * * * *